US012347555B2

(12) United States Patent
Monaghan et al.

(10) Patent No.: US 12,347,555 B2
(45) Date of Patent: Jul. 1, 2025

(54) SYSTEM AND METHOD FOR MEDICAL DEVICE COMMUNICATION

(71) Applicant: INVACARE CORPORATION, Elyria, OH (US)

(72) Inventors: Matthew E. Monaghan, Chagrin Falls, OH (US); Kevin R. Starkey, Centerville, OH (US)

(73) Assignee: Ventec Life Systems, Inc., Bothell, WA (US)

( * ) Notice: Subject to any disclaimer, the term of this patent is extended or adjusted under 35 U.S.C. 154(b) by 0 days.

(21) Appl. No.: 17/376,566

(22) Filed: Jul. 15, 2021

(65) Prior Publication Data

US 2023/0017775 A1 Jan. 19, 2023

(51) Int. Cl.
*G08B 21/04* (2006.01)
*A61M 16/10* (2006.01)
*G16H 40/67* (2018.01)

(52) U.S. Cl.
CPC .......... *G16H 40/67* (2018.01); *A61M 16/101* (2014.02); *A61M 2205/18* (2013.01);
(Continued)

(58) Field of Classification Search
USPC .............. 340/539.12, 539.2, 539.22, 539.25, 340/539.17, 546, 687, 691.2, 691.6, 692,
(Continued)

(56) References Cited

U.S. PATENT DOCUMENTS 4,127,395 A 11/1978 McKey et al.
4,144,037 A 3/1979 Armond et al.
(Continued)

FOREIGN PATENT DOCUMENTS

AU 1999015998 A 8/1999
AU 200072682 A1 5/2001
(Continued)

OTHER PUBLICATIONS

US 6,979,301 B2, 12/2005, Van Brunt et al. (withdrawn)
International Search Report and Written Opinion from Application No. PCT/US2022/037065 dated Oct. 25, 2022 (4 pages).
International Preliminary Report on Patentability from Application No. PCT/US2022/037065 dated Jan. 25, 2022 (9 pages).
Invacare XPO2 Portable TM Portable Oxygen Concentrator Brochure, 2010, 4 pages.
Invacare Platinum Mobile POC1-100B, POC1-100C en Oxygen Concentrator User Manual, 2018, 160 pages.
(Continued)

*Primary Examiner* — Daniel Previl
(74) *Attorney, Agent, or Firm* — Calfee, Halter & Griswold LLP

(57) ABSTRACT

Systems and methods are provided remotely controlling a medical device. In some embodiments, systems and methods are also provided for remote medical monitoring. This includes, for example, emergency/panic notifications/functions, medical event recording, compliance monitoring, sleep timer and environmental controls, two-way communication, and other functions such as, for example, emergency telephony/communication in various forms. In other embodiments, systems and methods for managing a remote control of a medical device are provided. This includes, for example, two-way communication for assisting in locating the remote, power management including sleep mode and wireless charging, and master remote/key functionality. The remote can be handheld or wearable and may include, for example, audio, visual, haptic, input, communication, and sensor (including biosensor) functionality and outputs. In this manner, the remote control can not only control the medical device, but also provides the user with extended functionality for emergency and non-emergency communication and tasks.

21 Claims, 13 Drawing Sheets

(52) U.S. Cl.
CPC ............... *A61M 2205/3553* (2013.01); *A61M 2205/502* (2013.01); *A61M 2205/581* (2013.01); *A61M 2205/582* (2013.01); *A61M 2205/583* (2013.01); *A61M 2230/04* (2013.01); *A61M 2230/20* (2013.01); *A61M 2230/40* (2013.01); *A61M 2230/50* (2013.01); *A61M 2230/63* (2013.01)

(58) Field of Classification Search
USPC .................................................. 340/825.19
See application file for complete search history.

(56) References Cited

U.S. PATENT DOCUMENTS

| | | |
|---|---|---|
| 4,247,311 A | 1/1981 | Seibert |
| 4,378,982 A | 4/1983 | Mcombs |
| 4,449,990 A | 5/1984 | Tedford |
| 4,454,596 A | 6/1984 | Wunsch et al. |
| 4,561,287 A | 12/1985 | Rowland |
| 4,575,042 A | 3/1986 | Grimland |
| 4,648,888 A | 3/1987 | Rowland |
| 4,826,510 A | 5/1989 | McCombs |
| 4,832,711 A | 5/1989 | Christel, Jr. et al. |
| 4,932,402 A | 6/1990 | Snook et al. |
| 4,971,609 A | 11/1990 | Pawlos |
| 5,057,822 A | 10/1991 | Hoffman |
| 5,099,837 A | 3/1992 | Russel et al. |
| 5,101,656 A | 4/1992 | Miller |
| 5,144,945 A | 8/1992 | Nishino et al. |
| 5,258,056 A | 11/1993 | Shirley et al. |
| 5,294,049 A | 3/1994 | Trunkle et al. |
| 5,298,226 A | 3/1994 | Nowobilski |
| 5,469,372 A | 11/1995 | McBrearty et al. |
| 5,474,595 A | 12/1995 | McCombs |
| 5,593,478 A | 1/1997 | Hill et al. |
| 5,626,131 A | 5/1997 | Chua et al. |
| 5,680,409 A | 10/1997 | Qin et al. |
| 5,720,276 A | 2/1998 | Kobatake et al. |
| 5,779,773 A | 7/1998 | Cam et al. |
| 5,785,681 A | 7/1998 | Indravudh |
| 5,906,672 A | 5/1999 | Michaels et al. |
| 5,917,135 A | 6/1999 | Michaels et al. |
| 5,931,160 A | 8/1999 | Gilmore et al. |
| 5,988,165 A | 11/1999 | Richey, II et al. |
| 6,051,051 A | 4/2000 | Hees et al. |
| 6,106,245 A | 8/2000 | Cabuz |
| 6,151,586 A | 11/2000 | Brown |
| 6,152,134 A | 11/2000 | Webber et al. |
| 6,266,995 B1 | 7/2001 | Scott |
| 6,279,377 B1 | 8/2001 | Cao |
| 6,419,630 B1 | 7/2002 | Taylor et al. |
| 6,427,690 B1 | 8/2002 | McCombs et al. |
| 6,442,433 B1 | 8/2002 | Linberg |
| 6,472,988 B1 | 10/2002 | Feld et al. |
| 6,517,610 B1 | 2/2003 | La Houssaye |
| 6,520,176 B1 | 2/2003 | Dubois et al. |
| 6,561,187 B2 | 5/2003 | Schmidt et al. |
| 6,629,525 B2 | 10/2003 | Hill et al. |
| 6,651,658 B1 | 11/2003 | Hill et al. |
| 6,691,702 B2 | 2/2004 | Appel et al. |
| 6,764,534 B2 | 7/2004 | McCombs et al. |
| 6,837,244 B2 | 1/2005 | Yagi et al. |
| 6,878,186 B2 | 4/2005 | Neary |
| 6,949,133 B2 | 9/2005 | McCombs et al. |
| 6,962,654 B2 | 11/2005 | Arnaud |
| 7,036,729 B2 | 5/2006 | Chung |
| 7,115,104 B2 | 10/2006 | Van Brunt et al. |
| 7,278,983 B2 | 10/2007 | Ireland et al. |
| 7,294,170 B2 | 11/2007 | Richey, II et al. |
| 7,306,657 B2 | 12/2007 | Yagi et al. |
| 7,329,304 B2 | 2/2008 | Bliss et al. |
| 7,331,340 B2 | 2/2008 | Barney |
| 7,393,382 B2 | 7/2008 | Givens |
| 7,425,203 B2 | 9/2008 | Van Brunt et al. |
| 7,431,032 B2 | 10/2008 | Jagger et al. |
| 7,445,663 B1 | 11/2008 | Hunter et al. |
| 7,455,717 B2 | 11/2008 | Sprinkle |
| 7,491,182 B2 | 2/2009 | Van Brunt |
| 7,552,731 B2 | 6/2009 | Jorczak et al. |
| 7,604,004 B2 | 10/2009 | Jagger et al. |
| 7,604,005 B2 | 10/2009 | Jagger et al. |
| 7,652,571 B2 | 1/2010 | Parkulo et al. |
| 7,662,638 B2 | 2/2010 | Dadala et al. |
| 7,686,870 B1 | 3/2010 | Deane et al. |
| 7,722,698 B2 | 5/2010 | Thompson et al. |
| 7,722,700 B2 | 5/2010 | Sprinkle |
| 7,753,996 B1 | 7/2010 | Deane et al. |
| 7,766,010 B2 | 8/2010 | Jagger et al. |
| 7,794,522 B2 | 9/2010 | Bliss et al. |
| 7,826,728 B2 | 11/2010 | Konno et al. |
| 7,866,315 B2 | 1/2011 | Jagger et al. |
| 7,875,105 B2 | 1/2011 | Chambers et al. |
| 7,922,789 B1 | 4/2011 | Deane et al. |
| 7,931,197 B2 | 4/2011 | Brandt et al. |
| 8,013,739 B2 | 9/2011 | Parkulo et al. |
| 8,062,003 B2 | 11/2011 | Goertzen et al. |
| 8,070,853 B2 | 12/2011 | Sprinkle |
| 8,092,396 B2 | 1/2012 | Bagha et al. |
| 8,231,541 B2 | 7/2012 | Colquitt et al. |
| 8,262,771 B2 | 9/2012 | Seki et al. |
| 8,366,402 B2 | 2/2013 | St. Michel |
| 8,366,815 B2 | 2/2013 | Taylor et al. |
| 8,377,181 B2 | 2/2013 | Taylor et al. |
| 8,421,465 B2 | 4/2013 | Carter |
| 8,547,062 B2 | 10/2013 | Carter et al. |
| 8,568,519 B2 | 10/2013 | Taylor et al. |
| 8,599,016 B2 | 12/2013 | Parkulo et al. |
| 8,668,767 B2 | 3/2014 | Sprinkle et al. |
| 8,677,998 B2 | 3/2014 | Yamaura et al. |
| 8,726,744 B2 | 5/2014 | Alburty et al. |
| 8,818,824 B2 | 8/2014 | DeBusk et al. |
| 8,956,289 B2 | 2/2015 | Kitajima et al. |
| 9,058,741 B2 | 6/2015 | Steinhauer et al. |
| 9,072,849 B2 | 7/2015 | Steinhauer et al. |
| 9,132,377 B2 | 9/2015 | Richey, II et al. |
| 9,266,053 B2 | 2/2016 | Shelnutt et al. |
| 9,317,660 B2 | 4/2016 | Burich et al. |
| 9,327,090 B2 | 5/2016 | Steinhauer et al. |
| 9,352,110 B2 | 5/2016 | Steinhauer et al. |
| 9,364,626 B2 | 6/2016 | Carter et al. |
| 9,440,179 B2 | 9/2016 | Wilkinson et al. |
| 9,460,262 B2 | 10/2016 | Kaufman et al. |
| 9,462,977 B2 | 10/2016 | Horseman |
| 9,693,734 B2 | 7/2017 | Horseman |
| 9,714,860 B2 | 7/2017 | Obenchain |
| 9,763,585 B2 | 9/2017 | Addison et al. |
| 9,782,557 B2 | 10/2017 | Wilkinson et al. |
| 9,788,735 B2 | 10/2017 | Al-Ali |
| 9,808,156 B2 | 11/2017 | Horseman |
| 9,833,142 B2 | 12/2017 | Horseman |
| 9,838,508 B2 | 12/2017 | Salem |
| 9,839,786 B2 | 12/2017 | Rondoni et al. |
| 9,872,623 B2 | 1/2018 | Al-Ali |
| 9,872,965 B2 | 1/2018 | Baloa et al. |
| 9,956,370 B2 | 5/2018 | Wilkinson et al. |
| 9,957,125 B2 | 5/2018 | Ray |
| 9,990,466 B2 | 6/2018 | DeBusk et al. |
| 10,004,435 B2 | 6/2018 | Larvenz et al. |
| 10,010,969 B2 | 7/2018 | Reed et al. |
| 10,037,044 B2 | 7/2018 | Laberge et al. |
| 10,058,269 B2 | 8/2018 | Lynn |
| 10,108,785 B2 | 10/2018 | Kamen et al. |
| 10,139,282 B2 | 11/2018 | Chrostowski |
| 10,179,217 B2 | 1/2019 | Steinhauer et al. |
| 10,252,037 B2 | 4/2019 | Degen et al. |
| 10,271,779 B2 | 4/2019 | Addison et al. |
| 10,349,901 B2 | 7/2019 | Osypka et al. |
| 10,357,628 B2 | 7/2019 | Jagger et al. |
| 10,391,019 B2 | 8/2019 | Stryker et al. |
| 10,426,904 B2 | 10/2019 | Broborg et al. |
| 10,496,788 B2 | 12/2019 | Amarasingham et al. |
| 10,521,720 B2 | 12/2019 | Detzler et al. |
| 10,592,637 B2 | 3/2020 | Velamuri et al. |
| 10,630,814 B2 | 4/2020 | Barnes et al. |

(56) References Cited

U.S. PATENT DOCUMENTS

| | | |
|---|---|---|
| 11,287,847 B2* | 3/2022 | Ritchey .................... H04N 7/18 |
| 2002/0053286 A1 | 5/2002 | Czabala |
| 2002/0096174 A1 | 7/2002 | Hill et al. |
| 2003/0068828 A1 | 4/2003 | Dadala et al. |
| 2003/0180164 A1 | 9/2003 | Bunner et al. |
| 2003/0215342 A1 | 11/2003 | Higashino |
| 2003/0231967 A1 | 12/2003 | Najafi et al. |
| 2004/0079359 A1 | 4/2004 | Aylsworth et al. |
| 2004/0167464 A1 | 8/2004 | Ireland et al. |
| 2005/0263199 A1 | 12/2005 | Meheen |
| 2006/0005842 A1 | 1/2006 | Rashad |
| 2006/0025932 A1 | 2/2006 | Dadala et al. |
| 2006/0086251 A1 | 4/2006 | Sprinkle |
| 2006/0174871 A1 | 8/2006 | Jagger et al. |
| 2006/0174872 A1 | 8/2006 | Jagger |
| 2006/0219245 A1 | 10/2006 | Holder |
| 2006/0220881 A1 | 10/2006 | Al et al. |
| 2006/0230929 A1 | 10/2006 | Bliss et al. |
| 2006/0251408 A1 | 11/2006 | Konno et al. |
| 2007/0032733 A1* | 2/2007 | Burton ................. A61B 5/7264 |
| | | 600/509 |
| 2007/0056584 A1 | 3/2007 | Jagger et al. |
| 2007/0140869 A1 | 6/2007 | St. Michel |
| 2007/0144519 A1 | 6/2007 | Henry et al. |
| 2007/0250017 A1 | 10/2007 | Carred et al. |
| 2008/0007396 A1 | 1/2008 | Parkulo et al. |
| 2008/0066616 A1 | 3/2008 | Sprinkle |
| 2008/0136652 A1 | 6/2008 | Vaisnys et al. |
| 2008/0238323 A1 | 10/2008 | Chan et al. |
| 2008/0246277 A1 | 10/2008 | Gallagher et al. |
| 2008/0257145 A1 | 10/2008 | Sprinkle |
| 2008/0262657 A1 | 10/2008 | Howell et al. |
| 2009/0065526 A1 | 3/2009 | Sprinkle |
| 2009/0118632 A1 | 5/2009 | Goepp |
| 2009/0126736 A1 | 5/2009 | Taylor et al. |
| 2009/0209839 A1 | 8/2009 | Ochs et al. |
| 2009/0211438 A1 | 8/2009 | Thompson et al. |
| 2009/0211448 A1 | 8/2009 | McClain |
| 2009/0216747 A1 | 8/2009 | Li et al. |
| 2009/0232706 A1 | 9/2009 | Dadala et al. |
| 2009/0240297 A1 | 9/2009 | Shavit |
| 2010/0063834 A1* | 3/2010 | Mukherjee ............. G16H 15/00 |
| | | 705/2 |
| 2010/0071698 A1 | 3/2010 | Kiritake |
| 2010/0095841 A1 | 4/2010 | Naheiri |
| 2010/0106458 A1 | 4/2010 | Leu |
| 2010/0114218 A1 | 5/2010 | Heath |
| 2010/0146426 A1 | 6/2010 | Parkulo et al. |
| 2010/0242734 A1 | 9/2010 | Maeda et al. |
| 2010/0253505 A1 | 10/2010 | Chou |
| 2010/0294127 A1 | 11/2010 | Dolensky |
| 2011/0017216 A1 | 1/2011 | Van Brunt et al. |
| 2011/0056904 A1 | 3/2011 | Rozenberg |
| 2011/0073107 A1 | 3/2011 | Rodman et al. |
| 2011/0126829 A1 | 6/2011 | Carter |
| 2011/0128008 A1 | 6/2011 | Carter |
| 2011/0315140 A1 | 12/2011 | Shuman |
| 2012/0036461 A1 | 2/2012 | Parkulo et al. |
| 2012/0184207 A1* | 7/2012 | Gaines ................ H04W 48/18 |
| | | 455/11.1 |
| 2012/0192864 A1* | 8/2012 | Galbraith ............... B01D 53/26 |
| | | 96/111 |
| 2012/0265591 A1* | 10/2012 | Hwang ................. G06Q 30/00 |
| | | 705/14.1 |
| 2013/0012788 A1 | 1/2013 | Horseman |
| 2013/0012789 A1 | 1/2013 | Horseman |
| 2013/0012790 A1 | 1/2013 | Horseman |
| 2013/0233168 A1 | 9/2013 | Richey, II |
| 2013/0264218 A1 | 10/2013 | Vinton et al. |
| 2013/0297330 A1 | 11/2013 | Kamen et al. |
| 2013/0333702 A1 | 12/2013 | Baloa et al. |
| 2014/0000604 A1 | 1/2014 | Steinhauer et al. |
| 2014/0000605 A1 | 1/2014 | Steinhauer et al. |
| 2014/0000607 A1 | 1/2014 | Steinhauer et al. |
| 2014/0000608 A1 | 1/2014 | Steinhauer et al. |
| 2014/0000609 A1 | 1/2014 | Steinhauer et al. |
| 2014/0002246 A1 | 1/2014 | Steinhauer et al. |
| 2014/0006041 A1 | 1/2014 | Steinhauer et al. |
| 2014/0006052 A1 | 1/2014 | Steinhauer et al. |
| 2014/0007405 A1 | 1/2014 | Chambers et al. |
| 2014/0049792 A1 | 2/2014 | Ha |
| 2014/0163335 A1 | 6/2014 | Horseman |
| 2014/0163336 A1 | 6/2014 | Horseman |
| 2014/0163337 A1 | 6/2014 | Horseman |
| 2014/0166003 A1 | 6/2014 | Van Brunt et al. |
| 2014/0188516 A1 | 7/2014 | Kamen et al. |
| 2014/0190348 A1 | 7/2014 | Richey, II et al. |
| 2015/0077245 A1 | 3/2015 | Kaufman et al. |
| 2015/0137997 A1 | 5/2015 | Huang |
| 2015/0164390 A1 | 6/2015 | Larvenz et al. |
| 2015/0174359 A1 | 6/2015 | Elliott et al. |
| 2015/0213224 A1 | 7/2015 | Amarasingham et al. |
| 2015/0234993 A1 | 8/2015 | Detzler et al. |
| 2015/0250960 A1 | 9/2015 | Broberg et al. |
| 2015/0362929 A1 | 12/2015 | Laberge et al. |
| 2016/0022971 A1 | 1/2016 | Degen et al. |
| 2016/0034042 A1* | 2/2016 | Joo .................... G02B 27/0093 |
| | | 345/633 |
| 2016/0037292 A1 | 2/2016 | King |
| 2016/0152430 A1 | 6/2016 | Ray |
| 2016/0193468 A1* | 7/2016 | Rondoni ............. A61N 1/37217 |
| | | 607/42 |
| 2016/0206838 A1 | 7/2016 | Steinhauer et al. |
| 2016/0275261 A1 | 9/2016 | Velamuri et al. |
| 2016/0303388 A1 | 10/2016 | Rondoni |
| 2016/0324425 A1 | 11/2016 | Addison et al. |
| 2016/0367197 A1 | 12/2016 | Addison et al. |
| 2016/0375218 A1 | 12/2016 | Sprinkle et al. |
| 2017/0000395 A1 | 1/2017 | Addison et al. |
| 2017/0000423 A1 | 1/2017 | Addison et al. |
| 2017/0011131 A1 | 1/2017 | Li et al. |
| 2017/0017767 A1 | 1/2017 | Flower et al. |
| 2017/0053077 A1 | 2/2017 | Osypka et al. |
| 2017/0080262 A1 | 3/2017 | Freres et al. |
| 2017/0119235 A1 | 5/2017 | Hyde et al. |
| 2017/0122774 A1* | 5/2017 | Quady .................. G01D 4/002 |
| 2017/0202728 A1 | 7/2017 | Stryker |
| 2017/0224231 A1 | 8/2017 | Al-Ali |
| 2017/0224233 A1 | 8/2017 | Al-Ali |
| 2017/0291708 A1 | 10/2017 | Buenting et al. |
| 2018/0014791 A1 | 1/2018 | Montgomery et al. |
| 2018/0092576 A1* | 4/2018 | Ambrósio ............ A61B 5/0004 |
| 2018/0156667 A1 | 6/2018 | Chrostowski |
| 2018/0192965 A1 | 7/2018 | Rose et al. |
| 2018/0271421 A1 | 9/2018 | Larvenz et al. |
| 2018/0308570 A1* | 10/2018 | Schmehl ................ G16H 15/00 |
| 2018/0314416 A1 | 11/2018 | Powderly et al. |
| 2018/0369532 A1 | 12/2018 | Nebrigic |
| 2019/0068760 A1 | 2/2019 | Barnes et al. |
| 2019/0134340 A1 | 5/2019 | Nebrigac |
| 2019/0143056 A1 | 5/2019 | Steinhauer et al. |
| 2019/0200577 A1 | 7/2019 | Kath |
| 2019/0374139 A1 | 12/2019 | Kiani et al. |
| 2020/0016605 A1 | 1/2020 | Nebrigac |
| 2020/0035348 A1 | 1/2020 | Sartor et al. |
| 2020/0060545 A1 | 2/2020 | Maher et al. |
| 2020/0064011 A1 | 2/2020 | Nakano |
| 2020/0077902 A1* | 3/2020 | Angle .................. A61B 5/1112 |
| 2020/0081856 A1 | 3/2020 | Kojima |
| 2020/0193806 A1* | 6/2020 | Finke ..................... H04L 67/12 |
| 2020/0222021 A1* | 7/2020 | Shah .................. A61M 16/0447 |
| 2021/0008309 A1 | 1/2021 | Birnkrant et al. |
| 2021/0069360 A1* | 3/2021 | Shane .................. A61L 2/0011 |
| 2021/0249010 A1* | 8/2021 | Tayshete ................ G10L 15/22 |
| 2022/0273960 A1* | 9/2022 | Hresko ................ A61N 1/3993 |

FOREIGN PATENT DOCUMENTS

| | | |
|---|---|---|
| AU | 748829 B2 | 6/2002 |
| AU | 200072387 A | 6/2002 |
| AU | 2008240038 A1 | 10/2009 |
| AU | 2010282150 A1 | 7/2012 |
| AU | 2012279039 A1 | 1/2014 |

(56) References Cited

FOREIGN PATENT DOCUMENTS

| | | |
|---|---|---|
| AU | 2012279044 A1 | 1/2014 |
| AU | 2012279110 A1 | 1/2014 |
| AU | 2013364131 A1 | 7/2015 |
| AU | 2013364131 A8 | 9/2015 |
| AU | 2013364131 A2 | 10/2015 |
| AU | 2014357428 B2 | 5/2019 |
| AU | 2013364131 B2 | 7/2019 |
| AU | 2018258679 A1 | 11/2019 |
| AU | 2018295533 A1 | 1/2020 |
| BR | 112015015024 A2 | 7/2017 |
| CA | 2310667 A1 | 6/1999 |
| CA | 2379697 A1 | 2/2001 |
| CA | 2438457 C | 2/2004 |
| CA | 2772539 A1 | 6/2004 |
| CA | 2683367 A1 | 10/2008 |
| CA | 2506292 C | 5/2012 |
| CA | 2839287 A1 | 1/2013 |
| CA | 2840969 A1 | 1/2013 |
| CA | 2840975 A1 | 1/2013 |
| CA | 2840984 A1 | 1/2013 |
| CA | 3016496 A1 | 1/2013 |
| CA | 2310667 C | 7/2013 |
| CA | 2772539 C | 4/2014 |
| CA | 2896086 A1 | 6/2014 |
| CA | 2933599 A1 | 6/2015 |
| CA | 2945137 A1 | 10/2015 |
| CA | 2982855 A1 | 11/2016 |
| CA | 2840979 C | 7/2018 |
| CA | 3050643 A1 | 7/2018 |
| CA | 3059209 A1 | 11/2018 |
| CA | 3069278 A1 | 1/2019 |
| CA | 2933599 C | 12/2019 |
| CA | 3016496 C | 1/2020 |
| CN | 87102164 | 11/1987 |
| CN | 2585215 Y | 11/2003 |
| CN | 1610516 A | 4/2005 |
| CN | 1697681 A | 11/2005 |
| CN | 1697682 A | 11/2005 |
| CN | 1780655 A | 5/2006 |
| CN | 2839861 A | 11/2006 |
| CN | 101506868 A | 8/2009 |
| CN | 101520690 A | 9/2009 |
| CN | 101681455 A | 3/2010 |
| CN | 101687134 A | 3/2010 |
| CN | 101873824 A | 10/2010 |
| CN | 1780655 B | 12/2010 |
| CN | 101520690 B | 7/2011 |
| CN | 101141567 B | 12/2012 |
| CN | 103448727 A | 12/2013 |
| CN | 103534664 A | 1/2014 |
| CN | 101543047 B | 2/2014 |
| CN | 103764021 A | 4/2014 |
| CN | 103781405 A | 5/2014 |
| CN | 103781409 A | 5/2014 |
| CN | 104235038 A | 12/2014 |
| CN | 204226229 U | 3/2015 |
| CN | 204394496 U | 6/2015 |
| CN | 104951225 A | 9/2015 |
| CN | 104969227 A | 10/2015 |
| CN | 105269352 A | 1/2016 |
| CN | 205237581 U | 5/2016 |
| CN | 205302544 U | 6/2016 |
| CN | 205344448 U | 6/2016 |
| CN | 205578301 U | 9/2016 |
| CN | 205578306 U | 9/2016 |
| CN | 106075696 A | 11/2016 |
| CN | 106102571 A | 11/2016 |
| CN | 106455927 A | 2/2017 |
| CN | 103477340 B | 3/2017 |
| CN | 106574784 A | 4/2017 |
| CN | 106793238 A | 5/2017 |
| CN | 106887110 A | 6/2017 |
| CN | 106913326 A | 7/2017 |
| CN | 106931478 A | 7/2017 |
| CN | 206459246 U | 9/2017 |
| CN | 206655848 U | 11/2017 |
| CN | 108348148 A | 7/2018 |
| CN | 105373219 B | 9/2018 |
| CN | 109171755 A | 1/2019 |
| CN | 110292696 A | 10/2019 |
| CN | 110431509 A | 11/2019 |
| CN | 110604580 A | 12/2019 |
| CN | 107430497 B | 3/2020 |
| CN | 111792030 A | 10/2020 |
| DE | 3723019 A1 | 1/1989 |
| DE | 29605889 U1 | 6/1996 |
| DE | 19936893 A1 | 2/2001 |
| DE | 10037227 A1 | 2/2002 |
| DE | 19936893 C2 | 8/2002 |
| DE | 102005042268 A1 | 5/2006 |
| DE | 102007021564 A1 | 11/2008 |
| DE | 202006020670 U1 | 7/2009 |
| DE | 102008016768 A1 | 10/2009 |
| DE | 102008030790 A1 | 12/2009 |
| DE | 102014103377 A1 | 9/2014 |
| DE | 102014103397 A1 | 9/2014 |
| DE | 102016116761 A1 | 3/2017 |
| DE | 102017204049 B3 | 5/2018 |
| DE | 102018115858 A1 | 1/2020 |
| EP | 0420620 A2 | 4/1991 |
| EP | 0885645 A2 | 12/1998 |
| EP | 1032906 A1 | 9/2000 |
| EP | 1157731 A1 | 11/2001 |
| EP | 0885645 B1 | 1/2005 |
| EP | 1661596 B1 | 5/2006 |
| EP | 1707928 A1 | 10/2006 |
| EP | 1895892 A1 | 3/2008 |
| EP | 1340071 B1 | 3/2009 |
| EP | 2136682 A1 | 12/2009 |
| EP | 2138060 A2 | 12/2009 |
| EP | 2197530 A2 | 6/2010 |
| EP | 2266093 A2 | 12/2010 |
| EP | 2729052 A1 | 5/2014 |
| EP | 2729054 A1 | 5/2014 |
| EP | 2729056 A1 | 5/2014 |
| EP | 2751751 A1 | 7/2014 |
| EP | 2773410 A1 | 9/2014 |
| EP | 2861139 A1 | 4/2015 |
| EP | 2895224 A1 | 7/2015 |
| EP | 0936362 A2 | 10/2015 |
| EP | 1636076 B1 | 12/2015 |
| EP | 2613838 B1 | 3/2016 |
| EP | 2138060 B1 | 6/2016 |
| EP | 3069279 A1 | 9/2016 |
| EP | 3082977 A2 | 10/2016 |
| EP | 3117355 A1 | 1/2017 |
| EP | 3129949 A2 | 2/2017 |
| EP | 1850917 B1 | 6/2017 |
| EP | 3282382 A1 | 2/2018 |
| EP | 3283165 A1 | 2/2018 |
| EP | 3286910 A1 | 2/2018 |
| EP | 3294120 A1 | 3/2018 |
| EP | 3316769 A1 | 5/2018 |
| EP | 3316770 A1 | 5/2018 |
| EP | 2729051 B1 | 6/2018 |
| EP | 3372910 A1 | 9/2018 |
| EP | 2058162 B1 | 1/2019 |
| EP | 2936362 B1 | 3/2019 |
| EP | 3578220 A1 | 12/2019 |
| EP | 3614946 A1 | 3/2020 |
| EP | 3616040 A1 | 3/2020 |
| EP | 3627261 A1 | 3/2020 |
| EP | 3634538 A1 | 4/2020 |
| EP | 3638557 A1 | 4/2020 |
| FR | 2865655 A1 | 8/2005 |
| FR | 2865655 B1 | 4/2006 |
| GB | 1270296 A | 4/1972 |
| IN | 201202311 P4 | 5/2013 |
| IN | 201504225 P4 | 7/2016 |
| IN | 201647029095 A | 10/2016 |
| IN | 201721043516 A | 12/2017 |
| IN | 201947043607 A | 11/2019 |
| JP | 3348956 B2 | 11/2002 |
| JP | 2004258828 A | 9/2004 |

(56) References Cited

FOREIGN PATENT DOCUMENTS

| | | |
|---|---|---|
| JP | 2005098571 A | 4/2005 |
| JP | 2006153337 A | 6/2006 |
| JP | 4088313 B2 | 5/2008 |
| JP | 2008531218 A | 8/2008 |
| JP | 2008209094 A | 9/2008 |
| JP | 4469972 B2 | 6/2010 |
| JP | 2010119762 A | 6/2010 |
| JP | 2010287576 A | 12/2010 |
| JP | 2011075223 A | 4/2011 |
| JP | 5020358 B2 | 9/2012 |
| JP | 5250037 B2 | 7/2013 |
| JP | 5275955 B2 | 8/2013 |
| JP | 2014523038 A | 9/2014 |
| JP | 2014523039 A | 9/2014 |
| JP | 2014524797 A | 9/2014 |
| JP | 2014225236 A | 12/2014 |
| JP | 2015007083 A | 1/2015 |
| JP | 5711389 B2 | 4/2015 |
| JP | 2016033154 A | 3/2016 |
| JP | 2016509284 A | 3/2016 |
| JP | 2016197422 A | 11/2016 |
| JP | 2017503571 A | 2/2017 |
| JP | 2017508532 A | 3/2017 |
| JP | 6144238 B2 | 6/2017 |
| JP | 2017105839 A | 6/2017 |
| JP | 2017130833 A | 7/2017 |
| JP | 2017143589 A | 8/2017 |
| JP | 2017146065 A | 8/2017 |
| JP | 06203634 B2 | 9/2017 |
| JP | 6252607 B2 | 12/2017 |
| JP | 06299785 B2 | 3/2018 |
| JP | 6310507 B2 | 4/2018 |
| JP | 2018511440 A | 4/2018 |
| JP | 2018122119 A | 8/2018 |
| JP | 6465155 B2 | 2/2019 |
| JP | 6483594 B2 | 3/2019 |
| JP | 2019082290 A | 5/2019 |
| JP | 6581667 B2 | 9/2019 |
| JP | 2019207684 A | 12/2019 |
| JP | 2020011074 A | 1/2020 |
| JP | 2021039536 A | 3/2021 |
| KR | 2009069335 A | 6/2009 |
| KR | 2014070553 A | 6/2014 |
| KR | 2014114422 A | 9/2014 |
| KR | 2015117092 A | 10/2015 |
| KR | 20150117092 A | 10/2015 |
| KR | 101816443 B1 | 1/2018 |
| KR | 2018009326 A | 1/2018 |
| KR | 101942785 B1 | 1/2019 |
| KR | 2019019180 A | 2/2019 |
| KR | 2019089405 A | 7/2019 |
| KR | 2019093380 A | 8/2019 |
| KR | 2019112507 A | 10/2019 |
| KR | 102072394 B1 | 2/2020 |
| KR | 2020031433 A | 3/2020 |
| KR | 102103631 B1 | 4/2020 |
| KR | 2020054445 A | 5/2020 |
| MX | 2010005090 A | 5/2010 |
| MX | 2014007304 A | 7/2014 |
| MX | 2015004842 A | 7/2015 |
| MX | 355476 B | 4/2018 |
| RU | 2015143725 A | 4/2017 |
| WO | 1997007439 A1 | 2/1997 |
| WO | 1998007930 A1 | 2/1998 |
| WO | 1998056488 A1 | 12/1998 |
| WO | 1998057165 A1 | 12/1998 |
| WO | 1999027483 A1 | 6/1999 |
| WO | 2001008752 A1 | 2/2001 |
| WO | 2004009161 A1 | 1/2004 |
| WO | 2005071372 A1 | 8/2005 |
| WO | 2006086415 A2 | 8/2006 |
| WO | 2006086472 A2 | 8/2006 |
| WO | 2006086522 A2 | 8/2006 |
| WO | 2006092635 A1 | 9/2006 |
| WO | 2006118654 A1 | 11/2006 |
| WO | 2007072385 A2 | 6/2007 |
| WO | 2013006627 A2 | 6/2007 |
| WO | 2007095266 A2 | 8/2007 |
| WO | 2008036159 A1 | 3/2008 |
| WO | 2008128250 A1 | 10/2008 |
| WO | 2008131338 A1 | 10/2008 |
| WO | 2009022320 A2 | 2/2009 |
| WO | 2009032540 A1 | 3/2009 |
| WO | 2009052704 A1 | 4/2009 |
| WO | 2009114249 A2 | 9/2009 |
| WO | 2009148646 A2 | 12/2009 |
| WO | 2011088539 A1 | 7/2011 |
| WO | 2011017778 A9 | 11/2012 |
| WO | 2012174420 A2 | 12/2012 |
| WO | 2013006615 A1 | 1/2013 |
| WO | 2013006632 A1 | 1/2013 |
| WO | 2013067223 A1 | 5/2013 |
| WO | 2013134645 A1 | 9/2013 |
| WO | 2013188013 A1 | 12/2013 |
| WO | 2014005106 A1 | 1/2014 |
| WO | 2014041104 A1 | 3/2014 |
| WO | 2014060726 A1 | 4/2014 |
| WO | 2014071145 A1 | 5/2014 |
| WO | 2014100687 A2 | 6/2014 |
| WO | 2014101824 A1 | 7/2014 |
| WO | 2015073459 A1 | 5/2015 |
| WO | 2015095532 A2 | 6/2015 |
| WO | 2015136502 A1 | 9/2015 |
| WO | 2015157575 A2 | 10/2015 |
| WO | 2016105552 A1 | 6/2016 |
| WO | 2016168119 A1 | 10/2016 |
| WO | 2016172469 A1 | 10/2016 |
| WO | 2016182853 A1 | 11/2016 |
| WO | 2017004068 A1 | 1/2017 |
| WO | 2017004069 A1 | 1/2017 |
| WO | 2017029396 A1 | 2/2017 |
| WO | 2017101747 A1 | 6/2017 |
| WO | 2017106636 A1 | 6/2017 |
| WO | 2017106644 A1 | 6/2017 |
| WO | 2017126392 A1 | 7/2017 |
| WO | 2017141774 A1 | 8/2017 |
| WO | 2017218295 A1 | 12/2017 |
| WO | 2018016852 A1 | 1/2018 |
| WO | 2018044959 A1 | 3/2018 |
| WO | 2018200865 A1 | 11/2018 |
| WO | 2018201067 A1 | 11/2018 |
| WO | 2018209112 A1 | 11/2018 |
| WO | 2019008529 A1 | 1/2019 |
| WO | 2019202390 A1 | 10/2019 |
| WO | 2019236759 A1 | 12/2019 |
| WO | 2020023186 A1 | 1/2020 |
| WO | 2020037375 A1 | 2/2020 |
| WO | 2020041785 A1 | 2/2020 |
| WO | 2020042639 A1 | 3/2020 |
| WO | 2020086528 A1 | 4/2020 |

OTHER PUBLICATIONS

Invacare SOLO2 TM Transportable Oxygen Concentrator User Manual, 2010, 52 pages.
Invacare Perfecto2 TM V Oxygen Concentrator Brochure, 2009, 2 pages.
Invacare Platinum™ 10L Oxygen ConcentratorIRC10LXO2 en HomeFill® System Compatible User Manual, 2016, 36 pages.
Invacare Platinum 10 Oxygen Concentrator Brochure, 2019, 2 pages.
International Search Report and Written Opinion from PCT/US21/41714 dated Nov. 15, 2021 (13 pages).
International Search Report and Written Opinion from PCT/US21/41710 dated Nov. 15, 2021 (16 pages).
International Search Report and Written Opinion from PCT/US21/41711 dated Oct. 21, 2021 (13 pages).
Chinh et al. "Simulation and Experimental Study of a Single Fixed-Bed Model of Nitrogen Gas Generator Working by Pressure Swing Adsorption", MDPI, Processes 2019, retrieved on Sep. 22, 2021, retrieved from <URL: https://www.mdpl.com/2227-9717/7/10/654/.

(56) References Cited

OTHER PUBLICATIONS

"RIDL, ""Audible Alerts and Visible Signals for the Inogen One GS"", Inogen One GS blog, Oct. 30, 2019. (12 pages)".
International Search Report and Written Opinion from PCT/US21/41717 dated Oct. 21, 2021.
International Search Report and Written Opinion from PCT/US2021/041718 dated Nov. 4, 2021.
International Search Report and Written Opinion from PCT/US2021/041719 dated Oct. 27, 2021.
International Search Report and Written Opinion from PCT/US2021/041712 dated Dec. 16, 2021.
Invitation to Pay Additional Fees from PCT/US21/41712 dated Oct. 6, 2021 (2 pages).

\* cited by examiner

SYSTEM AND METHOD FOR MEDICAL DEVICE COMMUNICATION

BACKGROUND

Many types of medical devices are provided for home use and home therapy. Examples of such medical devices includes respiratory machines, homecare beds, wheelchairs, etc. One type of respiratory machine provided to users is an oxygen concentrator. Oxygen concentrator systems provide elevated concentrations of oxygen to assist users in breathing.

Such systems are known to be either stationary, transportable, or portable. Stationary systems are intended to remain in one location such as, for example, a user's home, bedroom or living room. Transportable systems are intended to be moved from location to location and often include wheels or other mechanisms to facilitate movement. Portable systems are intended to be carried with the user such as, for example, via a shoulder strap or similar accessory.

These and other medical devices are located near the user such as, for example, in the same room or may be located in another room. Even when in the same room, the medical device may be located some distance away from the user. This may be because that is where the nearest electrical outlet is located or because the medical device may create a level of noise during operation. This situation requires the user to get up and walk to the medical device when turning the device on and off and/or making adjustments. However, most user's requiring medical devices such as oxygen concentrators, for example, have reduced strength and/or stamina and such movement may be difficult. Further yet, emergencies and/or medical incidents may occur in the user's home. It is desirable to address these and other aspects of providing medical care at home and/or a care facility.

SUMMARY

Systems and methods are provided remotely controlling a medical device. In some embodiments, systems and methods are also provided for remote medical monitoring. This includes, for example, emergency/panic notifications/functions, medical event recording, compliance monitoring, sleep timer and environmental controls, two-way communication, and other functions such as, for example, emergency telephony/communication in various forms. In other embodiments, systems and methods for managing a remote control of a medical device are provided. This includes, for example, two-way communication for assisting in locating the remote, power management including sleep mode and wireless charging, and master remote/key functionality. The remote can be handheld or wearable and may include, for example, audio, visual, haptic, input, communication, and sensor (including biosensor) functionality. Other embodiments are disclosed as well. In this manner, the remote control can not only control the medical device, but also provides the user with extended functionality for emergency and non-emergency communication and tasks. The remote can also provide locally available information to the user when the user is not close enough to the controlled unit or medical device to get such information as alarms, status, conditions, settings, dosage, usage, etc. The remote can provide information and feedback to its user visually, with audio cues, haptic or other sensory feedback.

BRIEF DESCRIPTION OF THE DRAWINGS

In the accompanying drawings which are incorporated in and constitute a part of the specification, embodiments of the invention are illustrated, which, together with a general description of the inventions given above, and the detailed description given below, serve to example the principles of these inventions.

DESCRIPTION

Figure 1:
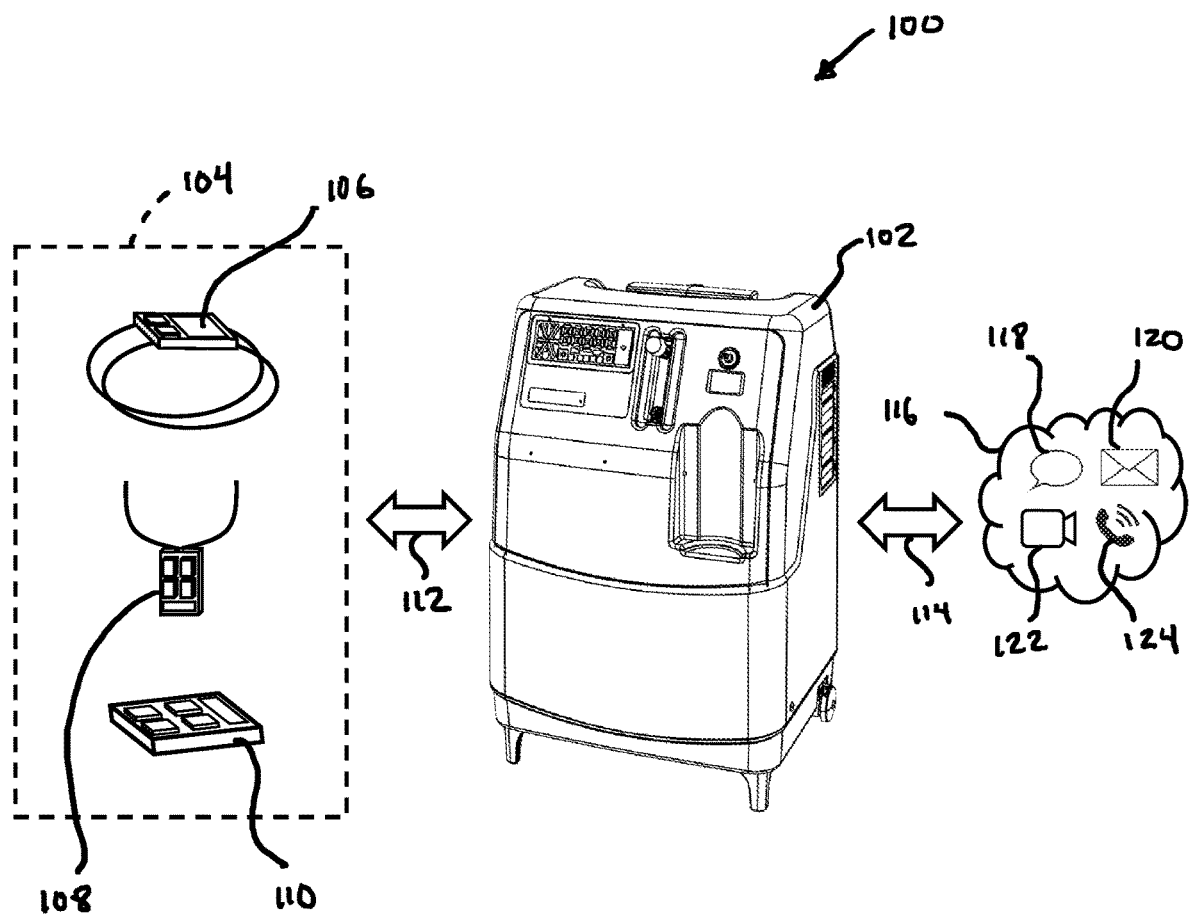
FIG. 1 shows one embodiment of a system and method for a remote control and a medical device.

Embodiments of the present inventions provide, for example, systems and methods for remote control and communication with a medical device and/or a (remote) network or system. The systems and methods can include, for example, a remote control that can be handheld and/or wearable. Wearable embodiments include, for example, pendant and wrist wearable remote controls. As will be described in more detail, the remote control can include, for example, a processor, memory and input and output devices such as buttons, lights, visual displays, audio speaker(s) and microphone(s), tactile or vibration device(s), communication modem(s) and radio(s), biosensor(s), accelerometer(s), gyroscope(s), light sensor(s), etc. and combinations of the foregoing.

In one embodiment, a system and method use a remote control having functionality for controlling the medical device and functionality for emergency and/or distress situations. Emergency and/or distress functions can include telephony or other network communication (wired or wireless) to provide audio, video, email, mobile app notifications, and/or text messages to local emergency services (i.e., 911 calls), medical provider and/or private call service, one or more family members, one or more friends, etc. and combinations of the foregoing. In another embodiment, the emergency and/or distress functions can include, for example, "man down" alarms that detect falls and/or impacts to a person. The "man down" alarms can include an audible local alert signal and be with or without telephony or other network communication distress messaging as described herein. In yet another embodiment, the emergency and/or panic functions can include a GPS-based distress signal emitted via very high radio frequency (VHF) or other type of powerful radio signal allowing emergency services to pick up the signal and locate its sender within a wider geographic area. In yet another embodiment, the emergency and/or panic functions can include sending a distress signal to a nursing and/or aide's station within a medical (or other care facility) and/or senior-living facility or community. In yet another embodiment, the emergency and/or panic functions can interface with a medical alert system already existing within the user's home, care, and/or living facility or community. By way of these examples and embodiments, the systems and methods can use a remote control, whether in combination with or without the medical device itself, to generate signals, data and information indicating an emergency and/or distress situation is present.

In another embodiment, the systems and methods use a remote control for indicating one or more medical events have occurred. For example, a user can create an input on the remote control to indicate one or more medical event(s) have occurred. This can, for example, create data indicating a timestamp (e.g., date and time) of the medical event(s). The medical event can be any medical event experienced by the user such as, for example, a respiratory event (e.g., breathing difficulty, asthma, coughing, congestion, etc.), cardiac event (e.g., irregular heartbeat, slow heartbeat, fast heartbeat, angina, etc.), fever, headache, sinus pain, etc. In other embodiments, the medical event data can further include biosensor data along with the time and date data. Biosensor data can include, for example, body temperature, EKG, heart beat/rate/variability, blood pressure, blood oxygen concentration, breathing rate, activity level, respiratory flow rate, respiratory volume, etc. In a further embodiment, the data also include medical device settings and diagnostic information such as, for example, flow settings, pressure settings, configuration settings, device usage (days, hours, minutes, seconds), device identification information, etc.

In another embodiment, the systems and methods use a remote control for inputting compliance monitoring information. For example, the systems and methods may prompt a user to provide input on a remote control during certain time intervals to confirm use and/or compliance with the therapy (e.g., oxygen therapy). The remote control can provide a cue or signal (e.g., a prompt) to the user indicating an input is required to confirm compliance. The cue or signal can include, for example, one or more of audio, visual, and/or tactile signals presented to the user. Upon such a prompt, the user can, for example, provide the compliance input by pressing or depressing a button on the remote control device indicating compliance with the therapy. In a further embodiment, the remote control device can include one or more prompts reminding the user that treatment or therapy should be begin. The prompt can be based or initiated on a timer indicating the device has not been used for a certain time period (e.g., hours, etc.) or a timer based on a particular time (e.g., time of day, week, etc.) indicating therapy or treatment should begin. In such a case, the remote control would generate a prompt to initiate treatment or therapy.

In yet another embodiment, systems and methods use a remote control for providing sleep timer signals for the medical device and/or controlling devices in the user's environment such as, for example, lights, thermostats, door locks, garage doors, televisions, radios, and other devices. The remote control can include sleep timer functionality for turning the associated medical device(s) off and/or on at the expiration of a set timer. For example, a remote control can set a time or sleep timer for turning off an oxygen concentrator medical device in, for example, 5, 10, 15, 20, etc. minutes. The remote control can also set a time or timer for turning on the medical device at a particular time or at the expiration of a timer. The logic for turning the medical device on and off based on time and timer data can be located either in the remote control or in the medical device itself. And, the remote control can transmit the time/timer data and/or on and off signals to the medical device to accomplish these functions. In some embodiments, the medical device will include the logic for receiving the time and/or timer data and configure itself to be turned on and/or off based on that data without further input from the remote control. In other embodiments, the remote control can directly turn the medical device on and/or off through transmission of such signals to the medical device based on the time and/or timer input by the user.

In yet further embodiments described herein, systems and methods are provided for locating a lost remote control, power and/or energy management of a remote control, charging the power source of a remote control, matching a paired remote control to a medical device within a warehouse setting, awakening from sleep mode a medical device stored in a warehouse upon receiving a signal from its paired remote control, and/or using a remote control as a master remote control that can communicate or be paired with any and/or all associated medical devices, including when a original remote control is lost for any one medical device.

Referring now to FIG. 1, one embodiment 100 of a system and method for a remote control and a medical device is illustrated. A medical device 102 and a remote control 104 therefore is provided. Medical device 102 can be, for example, any medical device suitable for remote control including respiratory machines (oxygen concentrators, nebulizers, CPAP's, ventilators, etc.), homecare/hospital beds, etc. The present embodiments illustrate an oxygen concentrator device as medical device 102 but the disclosure herein is not limited to such a device. Oxygen concentrators provide elevated concentrations of oxygen to assist users in breathing. Oxygen concentrating systems and methods are disclosed in, for example, U.S. Pat. Nos. 4,449,990, 5,906,672, 5,917,135, 5,988,165, 7,294,170, 7,455,717, 7,722,700, 7,875,105, 8,062,003, 8,070,853, 8,668,767, 9,132,377, 9,266,053, and 10,010,696 which are commonly assigned to Invacare Corporation of Elyria, Ohio and fully incorporated herein by reference.

Remote control 104 can be in any form including, for example, wearable 106 and 108 and handheld 110. Wearable forms include a wrist wearable 106 and/or a pendant wearable 108. Other forms are also possible. Remote control 104 can include, for example, a processor, memory and input and output devices such as buttons, lights, visual displays, audio speaker(s) and microphone(s), tactile or vibration device(s), communication modem(s) and radio(s), biosensor(s), accelerometer(s), gyroscope(s), light sensor(s), etc. and combinations of the foregoing. (See also, FIG. 13 and related description). Remote control 104 wirelessly communicates 112 with medical device 102 to accomplish a range of functions and processes, as described herein. The wireless communication can be, for example, optical (infrared), radio-frequency (Bluetooth, Wi-Fi, VHF, etc.), etc.

In one embodiment, the medical device 102 includes hardware and logic/software for sending data/information to a cloud network 116, which can include one or more remote servers, telephones, smart phones, computers, tablets, etc.) Medical device 102 communicates with the cloud network 116 via a wireless and/or wired communication 114. This can include for example, cellular, Bluetooth, Wi-Fi, VHF, LAN, ethernet, fiber optic, etc. communication. The data/information can include, for example, text messages 118, email messages 120, video 122, audio/voice 124, etc. (See also, FIG. 14 and related description).

Remote control 104 includes software and logic for controlling medical device 102. This includes, for example, on/off functions and/or operational settings. In the case of an oxygen concentrator, this can include on/off, modality (e.g., continuous or pulsed flow), oxygen flowrate settings (e.g., 0-5 liters per minute), sleep timer, wake timer, silence alarm(s), reset, etc. Remote control 104 includes one or more input devices such as, for example, buttons and/or a touchscreen, for receiving inputs from the user and transmitting them to the medical device for control thereof.

In one embodiment, remote control 104 includes emergency and/or distress communication and functionality. Remote control 104 includes one or more buttons or inputs the user can press when an emergency or distress situation occurs. This can be any medical situation including, for example, cardiac, pulmonary, circulatory, muscle, skeletal, neurological, psychological, mobility (e.g., falls or impacts to the body), etc. situations experienced by the user where the user is in some form of distress or in need of emergency assistance.

In one embodiment as shown in FIG. 1, remote control 104 transmits 112 the emergency or distress signal to medical device 102. Medical device 102 can then transmit 114 the emergency or distress signal via any one or more of its outputs including text messages 118, email messages 120, video messages 122, and/or audio or voice messages 124. These messages can be transmitted to any one or more of local emergency responders, medical providers, medical alert call service, family members, and/or friends. These messages can include any one or more of the following types of information including, for example, location, username and address, type of medical situation and/or distress and/or emergency, etc.

Medical device 102 can further include visual and audible distress indicators to further assist in the transmission and awareness of the emergency/distress signal. In a related embodiment, medical device 102 may only generate visual and/or audible distress indicators if cloud or network connectivity is not provided. The visual distress indicators can include, for example, one or more lights or displays flashing and/or providing visual cues, icons, or messages. The audible distress indicators can include, for example, buzzing, alarm, and/or chirp sounds indicative of an emergency and/or distressful situation.

Figure 2:
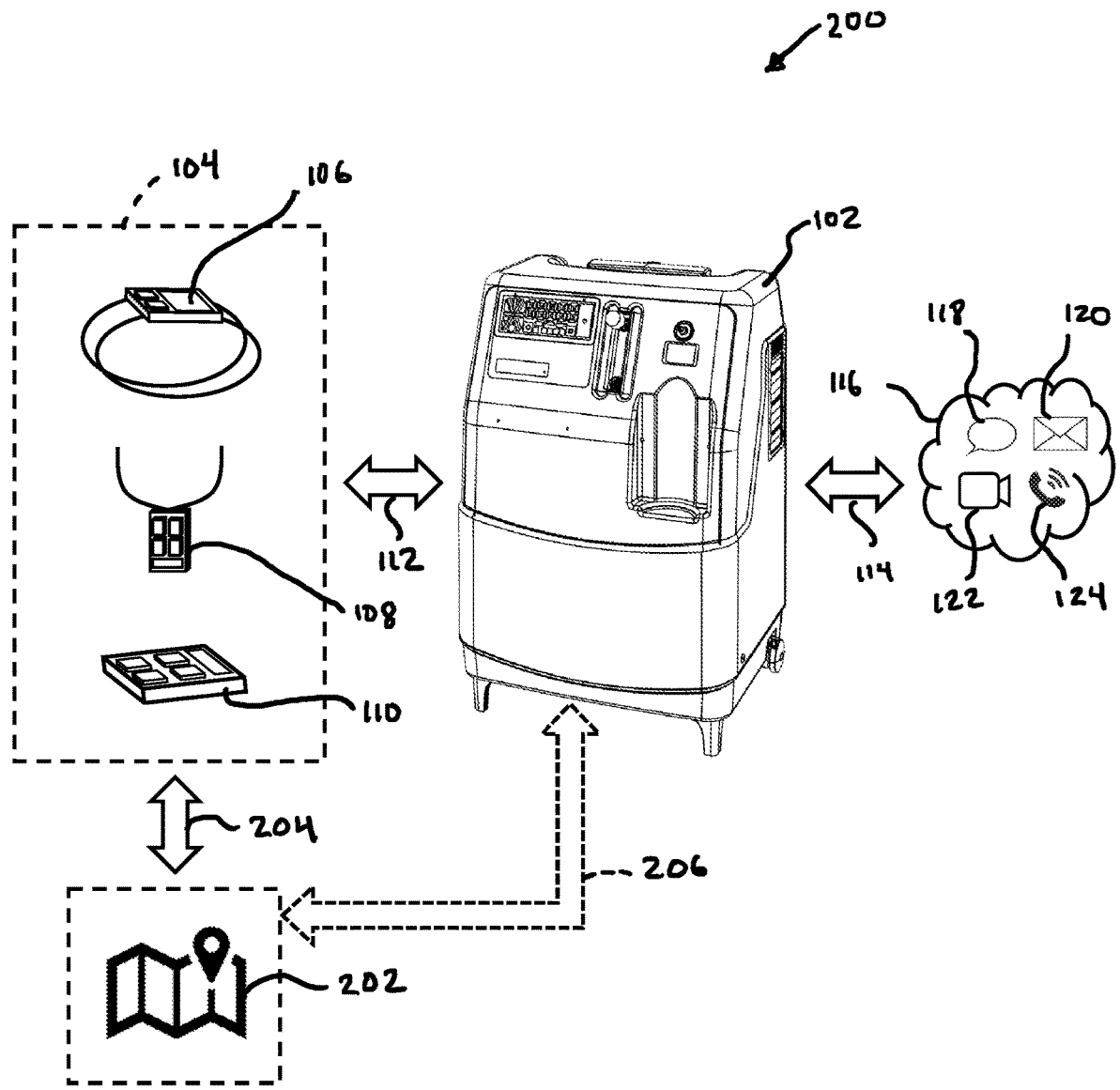
FIGS. 2-4 illustrate various embodiments of systems and methods for a remote control and medical device having emergency communication and functionality.

Referring now to FIG. 2, another embodiment 200 of a system and method for a remote control and medical device having emergency communication and functionality is illustrated. In this embodiment, a GPS-based distress signal 202 is generated. The signal includes GPS data/information to help locate the user in distress. The GPS-based distress signal 202 can be transmitted 204 wirelessly including, for example, via any radio-frequency (e.g., Bluetooth, Wi-Fi, VHF, UHF, etc.) In one embodiment, GPS-based distress signal 202 can be generated and transmitted 204 by remote device 104 upon user initiation (e.g., pressing a distress button, initiating a distress function) or automatically generated upon predetermined conditions (e.g., the user fell down, the user has stopped moving for a significant period of time, the users vital functions are low or at critical levels, etc.) In a related embodiment, the GPS-based distress signal 202 can be generated and transmitted 206 by medical device 102 in response to the user transmitting a distress or emergency situation via remote control 104 or any of the aforementioned conditions. Medical device 102 can also generate a distress signal and transmit 114 it to the cloud network 116. The GPS-based distress signal 202 has the advantage of providing the GPS location of the user to assist local emergency responders, medical providers, medical alert call services, family members, and/or friends in locating the user.

Figure 3:
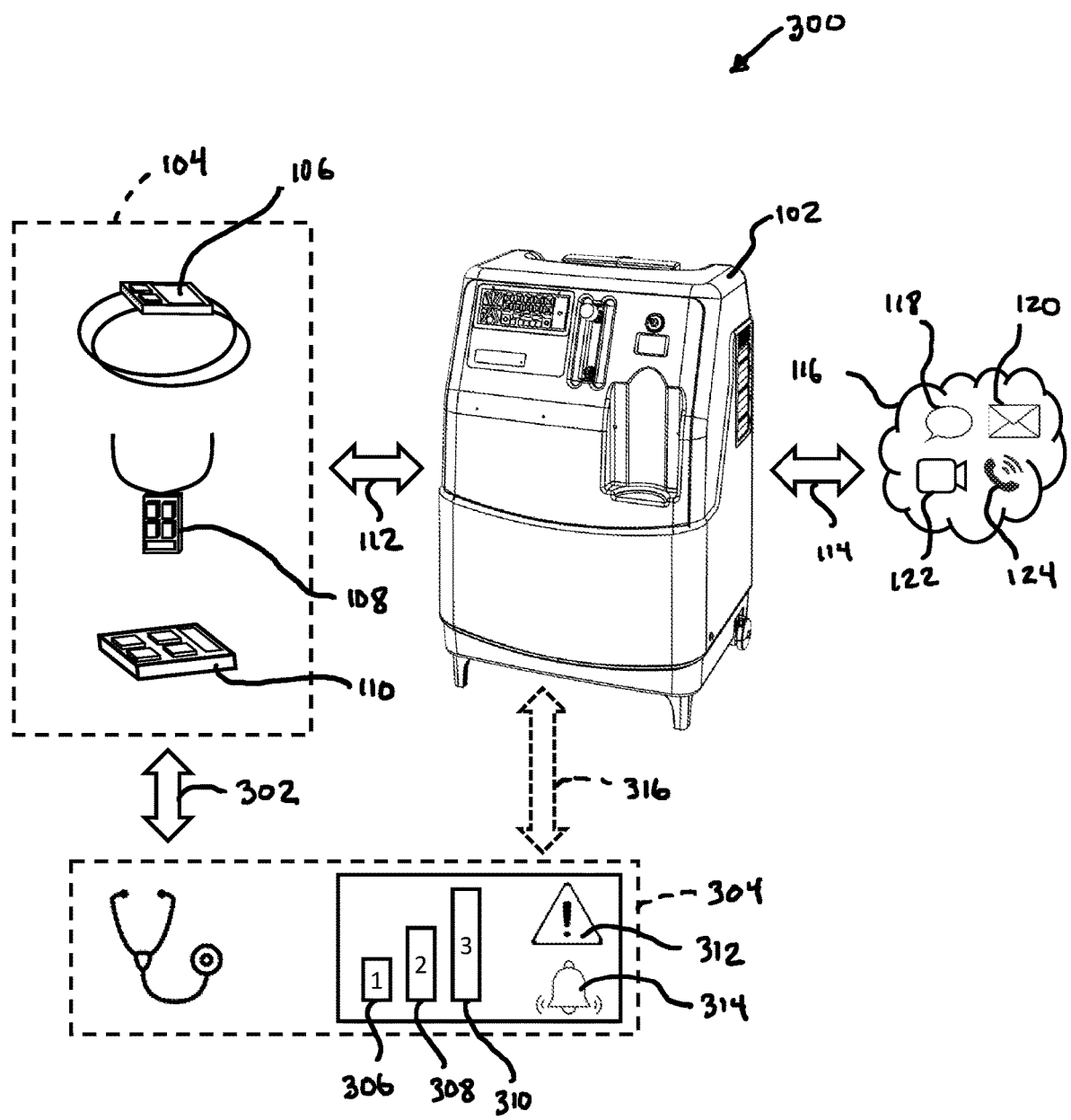

FIG. 3 illustrates an embodiment 300 of a system and method for remote control and medical device having emergency communication and functionality within an assisted living or medical care environment. In this embodiment, an emergency/distress signal is generated and can be transmitted 302 by a remote 104 to a nursing/aide's station 304. The user can generate the emergency/distress signal by, for example, any of the methods or conditions previously described. The distress/emergency signal can include, for example, information identifying the patient and/or their location within the facility or environment.

The nursing/aide's station 304 (and/or receiver) can also include logic for prioritizing the emergency/distress signal within other alarms integrated or otherwise generated at the nursing/aide's station by other systems. For example, the emergency/distress signal can be prioritized to have low, medium, or high priority (e.g., see bar icons/displays 306 (low), 308 (medium), 310 (high)). A high priority can place the emergency/distress signal above, for example, a general assistance or similar signal that may be received by the nursing/aide's station 304. A low or medium priority can place the emergency/distress signal below, for example, a trauma or other similar signal at the station.

The nursing/aide's station 304 can include a receiver having one or more alarms 312 and/or 314. Alarm 312 can include, for example, a visual alarm such as a message, display, and/or indicator light. The visual alarm 312 can also be colorized for priority. For example, yellow can indicate a low priority. Orange can indicate a medium priority. And, red can indicate a high priority. Other colors and indicators/cues including blinking or flashing may also be used alone or in combination with the foregoing.

Alarm 314 can include one or more audio, visual, haptic and/or other sensory feedback. Examples include an audio alarm such as a buzzer, tone, a plurality of tones, and/or voice. Audio alarm 314 can also include priority cues including slow repeat rate tone(s) for low priority alarms, a medium repeat rate tone(s) for medium priority alarms, and a high repeat rate tone(s) for high priority alarms. Audio alarm 314 can further include escalating volume, intensity, and/or duration for any of the above conditions. Other examples include haptic cues such as vibrations and/or pattern of vibrations or haptic pulses. For example, the patterns of vibrations or haptic pulses can be sequenced to designate certain information. A single pulse or vibration can represent patient 1, room 1, or alarm level 1, two pulses or vibrations can represent patient 2, room 2, or alarm level 2, etc. Similarly, the sequence an include long and/or short vibrations or haptic pulses. A long pulse, followed by a short pulse, followed by another long pulse, can represent patient 101, room 101, or alarm level 101, etc. The use of haptic feedback provides a discreet notification option. In these ways, a nurse or aide can see, hear, and/or feel the priority of the alarms and emergency/distress signals from remote device 104 and decide what is the appropriate action needed based on the information represented by the sensory feedback.

As previously described in connection with FIG. 2, medical device 102 can be triggered by remote device 104 to generate and transmit 316 an emergency/distress signal to nurse/aide's station 304. Medical device 102 can also transmit the signal to the cloud network 116. In this manner, the emergency/distress signal can be transmitted to multiple places for assistance or attention.

Figure 4:
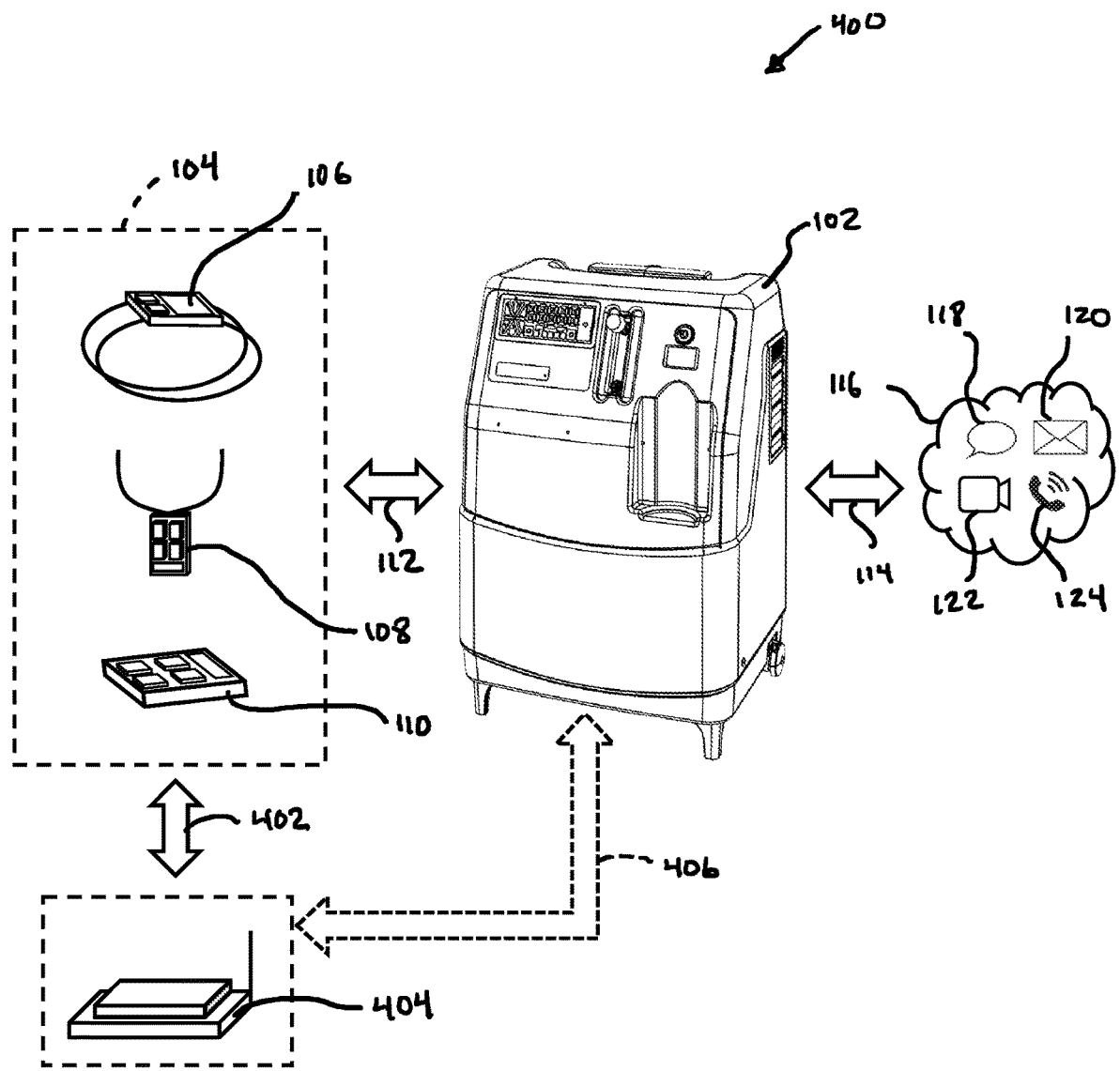

FIG. 4 illustrates an embodiment 400 of a system and method for remote control and medical device having emergency communication and functionality that communicates with a medical alert system 404. A medical alert system includes, for example, an alarm system that can generate a signal indicating the presence of a hazard or emergency requiring immediate attention and can call and/or message emergency medical personal, an emergency service, family members and/or friends. Remote device 404 can generate and transmit 404 an emergency/distress signal to medical alert system 404 according to any of the previously described methods and means. Also, medical device 102 can generate and transmit 406 an emergency/distress signal to medical alert system 404 either on its own or based on receipt of such a signal from medical device 104. This is accomplished by pairing remote device 104 and/or medical device 102 to medical alert system 404 so they can communicate with each other. In this manner, medical alert system 404 can be triggered to call and/or message for help or assistance using its own services.

Figure 5:
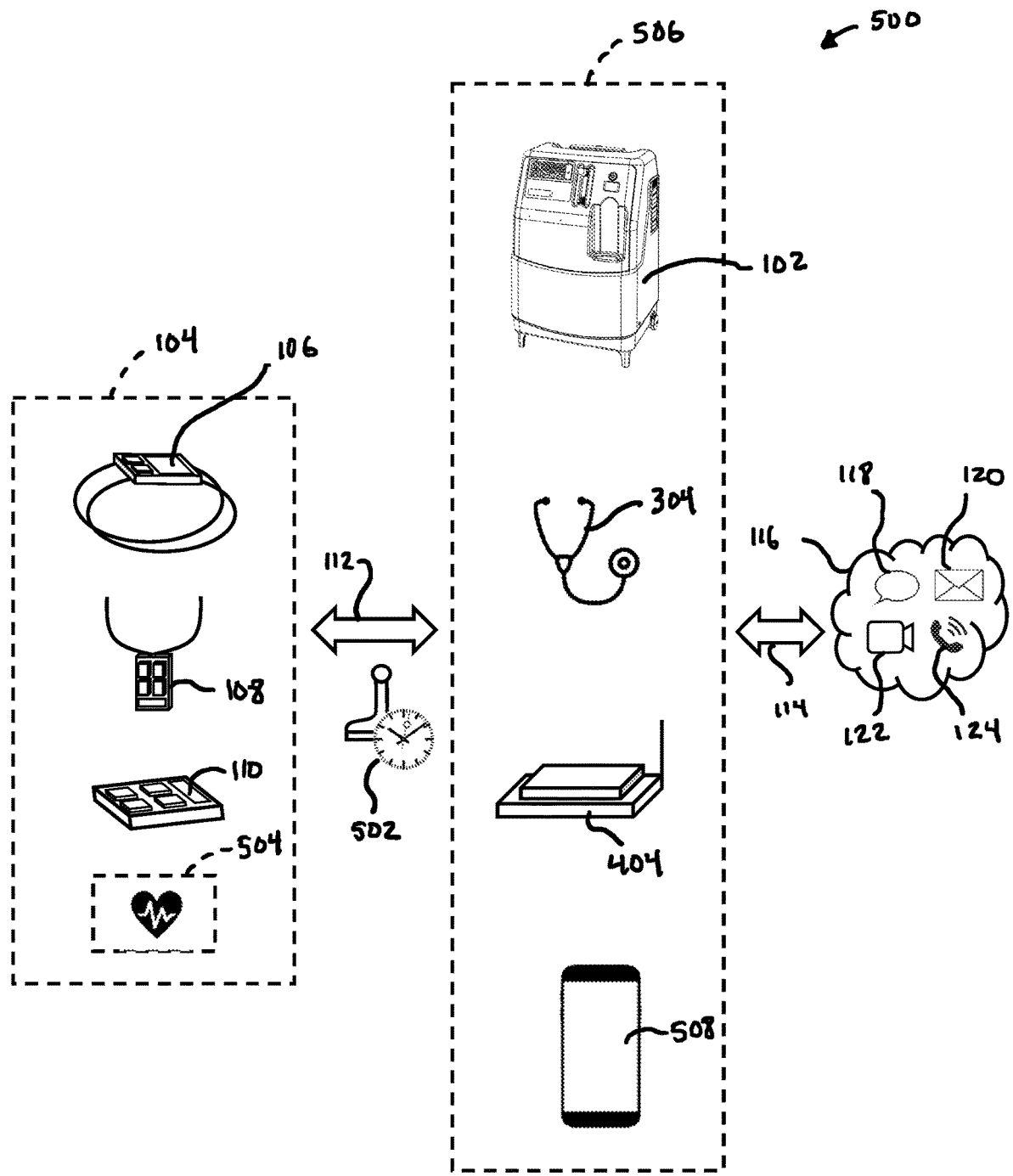
FIG. 5 is one embodiment of a system and method for a remote control and medical device having medical event recording and communication functionality.

Referring now to FIG. 5, one embodiment 500 a system and method for medical event recording is illustrated. Medical event information 502 is generated by remote device 104 to indicate a medical event has occurred. Medical event information 502 can be transmitted 112 to a receiving device 506 that can be, for example, medical device 102, nurse/aide's station 304, medical alert system 404, smart phone/tablet 508, etc. In a further embodiment, the receiving device 506 can transmit 114 the medical event information 502 to cloud network 116 or save it to internal memory for later retrieval, transmission, and/or analysis.

In one embodiment, the medical event information 502 can include a timestamp of when the medical event occurred. This information can include, for example, year, month, day, hour, minute, and/or second of occurrence. In other embodiments, this information can further include biosensor data such as for example electrocardiogram (EKG), blood pressure, blood oxygen level, heart rate (and other cardiac measurements), breathing rate and airway occlusions (including partial) (and other pulmonary measurements), etc. One or more of these sensors are either part of remote device 104 or communicate with remote device 104 to provide the sensor data information (see e.g., FIG. 13, biosensors 1324). Therefore, medical event information 502 can include timestamp and sensor data/information.

In operation, the user can provide an input such as, for example, depressing a button or other input, on remote device 104 to indicate a medical event has occurred. Examples of medical events include breathing issues (e.g., asthma, shortness of breath, difficulty breathing, etc.), cardiac issues (e.g., pain in the chest, fast heartbeat, slow heartbeat, heart attack, etc.), headaches, dizziness, etc. In one example, the user may depress a "medical event" button on remote device 104 each time the user experiences a cardiac issue. Logic within remote device 104 creates a timestamp of the event and, as described previously, may further record some or all of the associated biosensor data/information. In another example, the user may depress the "medical event" button on remote device 104 each time the user experiences a pulmonary or breathing issue. This medical event information 502 can then be transmitted to, for example, medical device 102, nurse/aide's station 304, medical alert system 404, smart phone/tablet 508, etc. and then further to cloud network 116 where a medical service provider, physician's office, hospital, etc. can receive the information for use in the care of the user.

Figure 6:
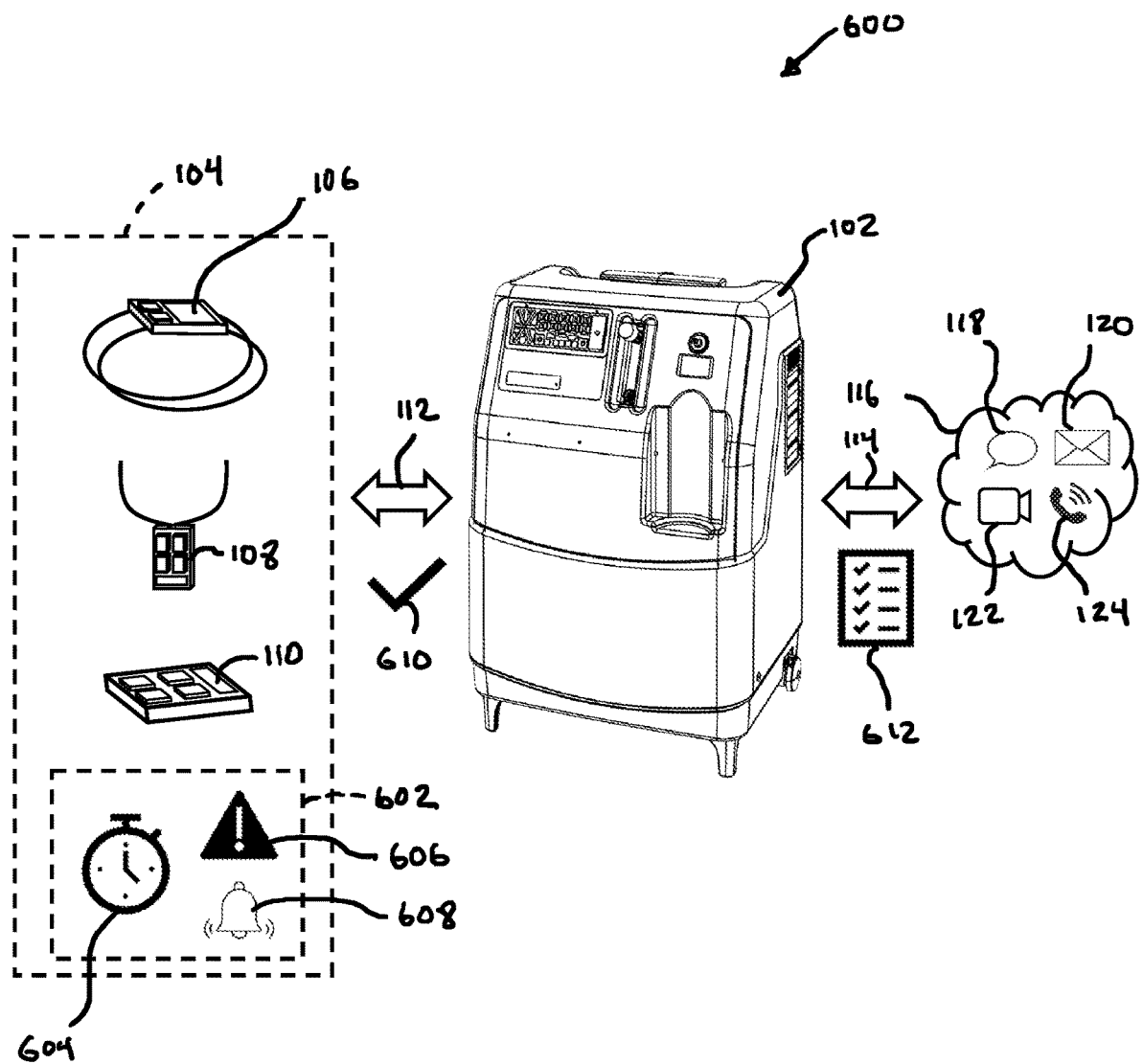
FIG. 6 is one embodiment of a system and method for a remote control and medical device having compliance monitoring and communication functionality.

FIG. 6 illustrates one embodiment 600 of a system and method for monitoring user compliance in, for example, use of the medical device or therapy provided by the medical device. Remote device 104 can include a compliance input such as, for example, a button, that the user must press during a time interval to indicate compliance in using the medical device 102 or the therapy provided thereby. For example, if the medical device 102 is an oxygen concentrator and the therapy is breathing with elevated oxygen concentration levels, the user may be required to press the "compliance" button, or submit a blood oxygen saturation measurement via a sensor or paired sensing device, during certain time intervals 604 (e.g., every 30 minutes) to signal or indicate compliance with the therapy. Logic 602 can be provided that generates an audio 608 and/or visual 606 cue to the user that it is time 604 to provide a compliance input (e.g., by for example pressing a compliance button or other input on remote device 104). Thus, for example, 3 hours of therapy can require 6 compliance inputs by the user (e.g., one compliance input on cue every 30 minutes). Other time intervals 604 can also be chosen.

Visual cues 606 can include, for example, a display, message, illuminated or flashing input or button, etc. Audio cues 608 can include, for example, a buzzer, tone, tones, and/or voice sounds indicating a compliance input is required. A compliance input by the user shuts off the visual/audio cue until the next time interval 604 expires and the user is prompted by the cues to provide a compliance input. Logic 602 also generates and collects compliance data 610 in regard to the user input. For example, compliance data 610 can include the total amount of therapy time indicated by user compliance inputs. If the compliance interval is, for example, every 30 minutes, then each user input will add 30 minutes of compliance time to the total.

In other embodiments, compliance data can further include date and/or time information such as, for example, year, month, day, hour, minute, and/or second. This allows the compliance data 610 to indicate with detail the compliance usage including duration and pattern of usage (monthly, weekly, time of day/night, etc.) Compliance data 610 can be transmitted 112 to medical device 102 for storage or further transmission (including bulk user compliance data 612) to cloud network 116 where a provider, insurer, physician's office, hospital, etc. can receive the information for assessment and care of the user.

Compliance logic 602 can reside either in remote device 104 or medical device 102. In the case of medical device 102, a signal can be transmitted 112 to remote device 104 to cue the user to provide a compliance input that would generate a signal back to medical device 102 that a compliance input has been made. In other embodiments, logic 602 and the compliance input may reside on the medical device 102 itself in the same manner as if presented on remote device 104. In yet other embodiments, both devices may include the logic to allow the user full flexibility in providing the compliance input on whichever device is physically closest to the user.

Figure 7:
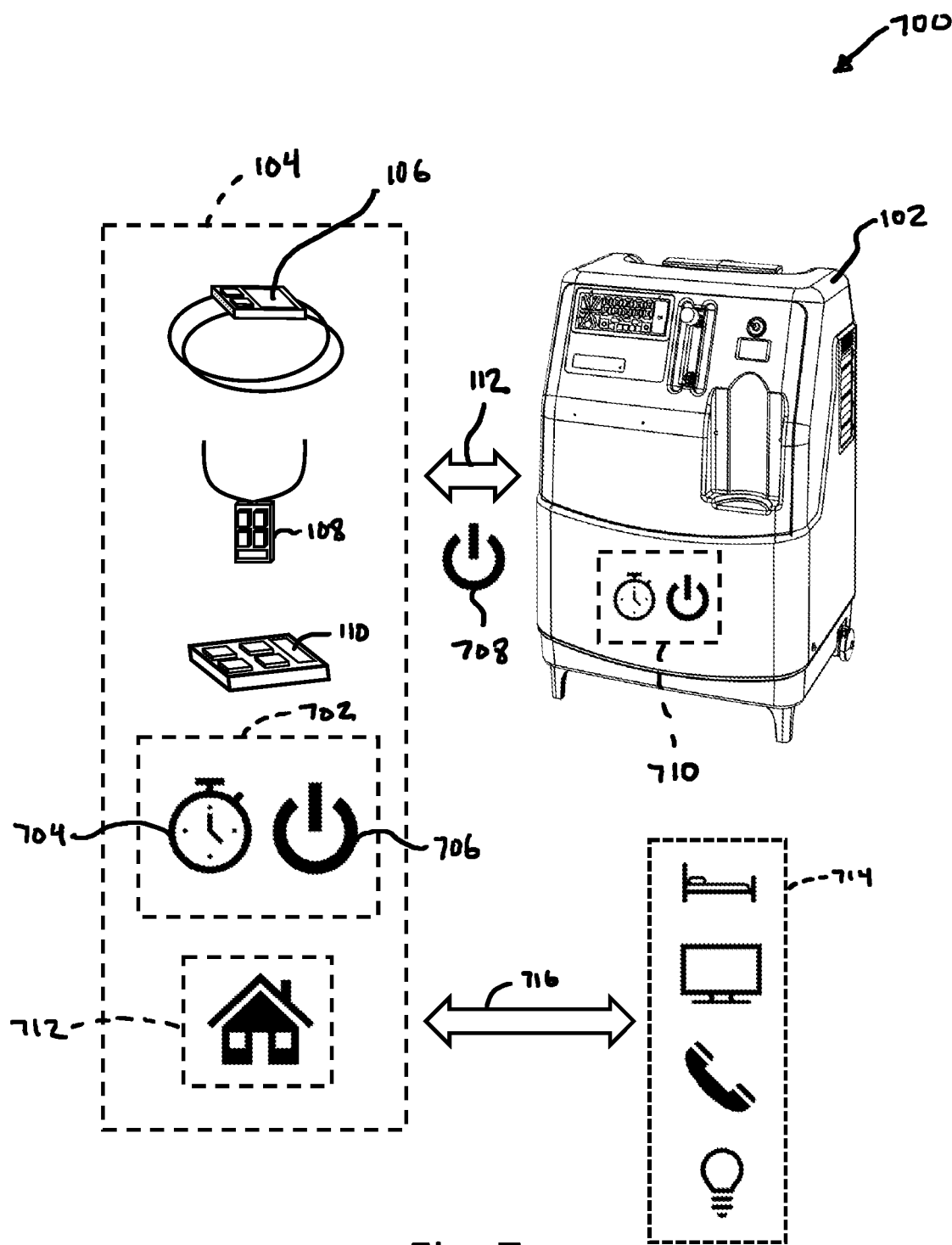
FIG. 7 is one embodiment of a system and method for a remote control and medical device having sleep-timer and environmental control and communication functionality.

FIG. 7 illustrates one embodiment 700 of a system and method for power management. In this embodiment, logic 702 can provide for one or more sleep timers 704 and associated on/off functions 706. Sleep timer 704 can be used to set a timer for how long medical device 102 operates before automatically shutting down/off. In one embodiment, sleep timer 704 has several possible durations (e.g., 30 minutes, one hour, two hours, etc.) that are input on remote device 104. The input can be via, for example, a sleep timer button that is repeatedly pressed to change the duration of the sleep timer 704. Remote device 104 transmits the sleep timer duration/setting 708 to medical device 102. The sleep timer settings can include a value entered by the user on remote device 104 (which value may also be changed in the same manner) of the duration of the timer after which the medical device 102 will either start or stop operation. Medical device 102 can include similar logic 710 for receiving and implementing the received sleep timer duration/setting 708. Medical device 102 can itself include a similar sleep timer input/button for setting the sleep timer duration without use of remote device 104. In this manner, a user may remotely and/or locally set a sleep timer for medical device 102, which conserves energy and component wear and tear.

Still referring to FIG. 7, one embodiment 700 of a system and method for environmental control is illustrated. Remote device 104 includes logic 712 for controlling one or more devices 714 in the environment (e.g., house, room, etc.) of the user. These devices 714 can include, for example, articulating beds (raise, lower, etc.), telephones (answering, dialing, hanging up, etc.), televisions and radios (on/off, channel and volume control, etc.), doors and windows (open, close, lock, etc.), lighting (on, off, dim, etc.), heating/air conditioning (on, off, temperature, etc.), computers/tablets (click, select, enter, mouse control, etc.) and small appliances (on, off, etc.) Remote device 104 can include one or more selector input(s) and logic for selecting which device(s) is to be controlled and one or more additional inputs and logic for controlling the selected device(s) by generating any of the example aforementioned control functions or signals. These inputs can be in the form of, for example, buttons and/or touchscreen menus and inputs. Depressing one or more of these inputs on remote device 104, the logic 712 generates and transmits 716 signals to control device(s) 714. These signals include on/off, increase/decrease, and any of the one or more functions noted above with respect to the example devices listed. In one embodiment, environmental devices 714 have an interface/receiver unit electrically and/or physically connected thereto for receiving the remote control 104 signals and translating them into physical or electrical functions associated with the environmental devices 714. This unit may take form of a wired or wireless receiver having logic to decode the input signal into a target device to control and a control signal. The unit can include relay-type outputs for providing a power control signal and/or digital outputs for providing digital control signals to the target device. This allows the user to control their environmental devices 714 and/or medical devices 102 from a single remote device.

Figure 8:
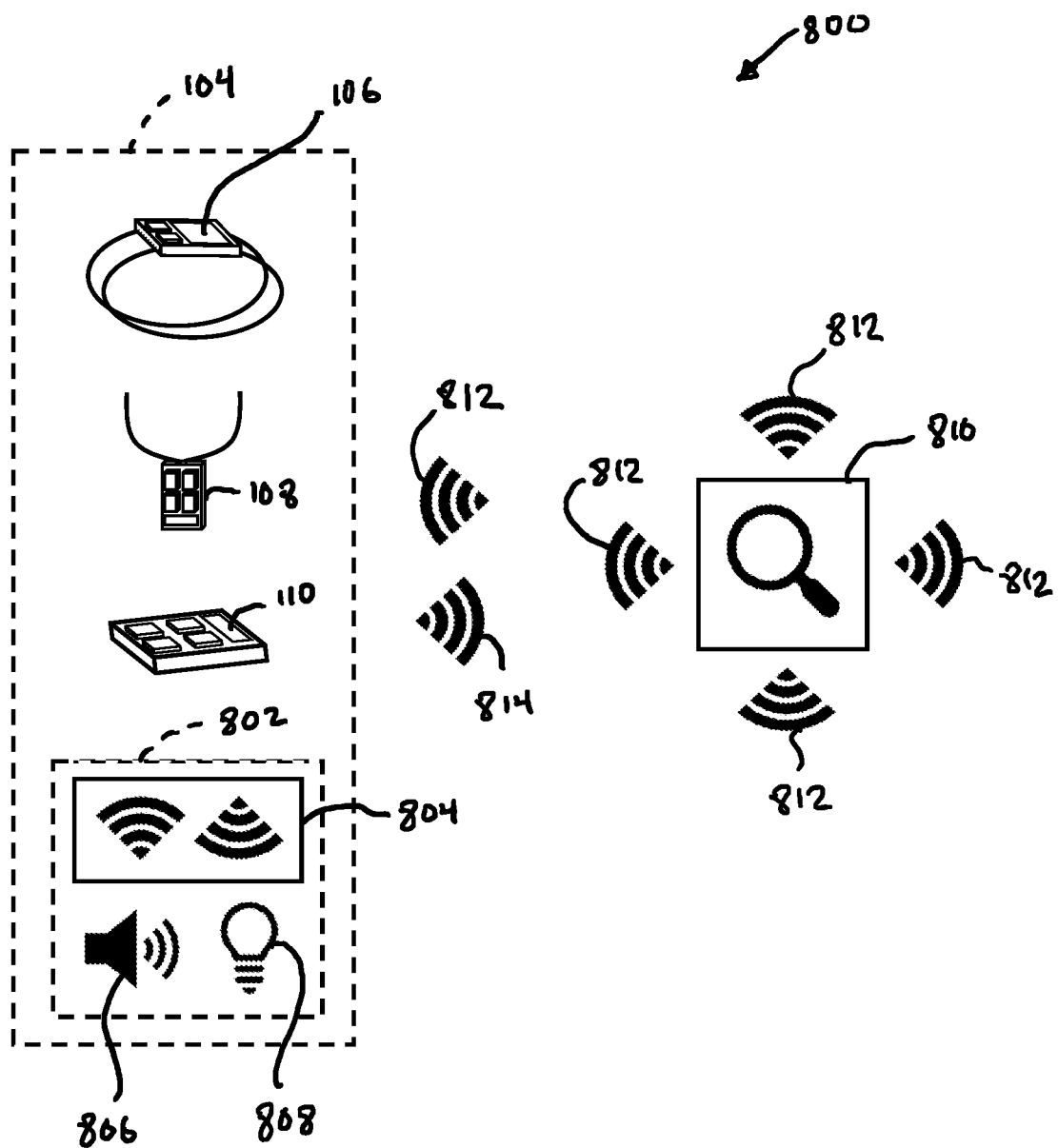
FIG. 8 is one embodiment of a system and method for a remote control and medical device having location assist and communication functionality.

FIG. 8 illustrates one embodiment 800 of a system and method for locating a remote device 104. Remote device 104 can include logic 802 receiving and transmitting lost and found signals 804. In one embodiment, a locating device 810 is used to emit a signal 812 that remote device 104 recognizes as a lost and found search signal. Upon receiving signal 812, logic 802 can generate and respond with audio 806 and/or visual 808 signals in order to assist in physically locating remote device 104. The audio 806 signal can be beep(s), tone(s) or any other audio. The visual signal 808 can be any illuminated display including, for example, flashing, strobing, color, etc. displays. Further yet, logic 802 can generate and transmit an acknowledgment signal 814 indicating remote device 104 has received the lost and found signal 812 from locating device 802. In one embodiment, acknowledgement signal 814 can include GPS information to assist in finding remote device 104. In this manner, when remote device 104 is lost, it can be located.

Figure 9:
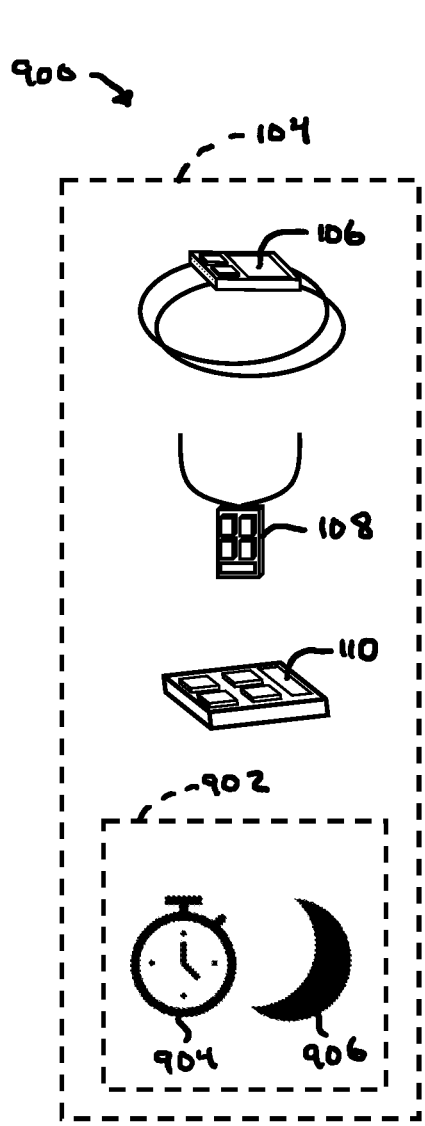
FIG. 9 is one embodiment of a system and method for a remote control and medical device having sleep mode functionality.

Referring now to FIG. 9, another embodiment 900 of a system and method for power management is illustrated. Remote device 104 can include logic 902 for conserving battery power. This includes timer logic 904, which sets a timer for putting remote device 104 into a sleep or energy saver mode. Sleep or energy saver mode suspends all nonessential processes/logic within remote device 104 (e.g. biosensor monitoring, GPS updating, user activity/fall sensing (e.g., accelerometer monitoring), etc.)

However, for example, sleep or energy saver mode does not suspend processes/logic for lost and found (e.g., logic 802, FIG. 8), input scanning to "wake" (e.g., such as a random button press to "wake" remote device 104 from sleep or energy mode), and emergency distress signal inputs (e.g., FIGS. 1-4), etc. Therefore, remote device 104 does not have to be "awoken" for the lost and found functionality/logic (e.g., FIG. 8) and/or emergency/distress signal logic (e.g., FIGS. 1-4) to be operational. That logic can, but does not have to be, deemed essential so as to not be suspended during sleep or energy saver mode. Other logic too can be deemed essential based on the user's preferences so as to not be suspended.

Timer logic 904 can be a repeating background process with a fixed time interval that resets upon any input (e.g., a button depression) provided by the user to remote device 104. For example, the fixed time interval may be 5 minutes (or any other time interval) and is reset each time the user depresses a button or other input on remote device 104. If there is no user input within the 5 minute time interval, logic 904 causes remote device 104 to enter sleep or energy saver mode whereby nonessential processes (e.g., as described above) are suspended.

Logic 902 can also include sleep logic 906 that allows the user to designate a time period within which remote device 104 will automatically enter sleep or energy saver mode at the expiration thereof. The time period can be any time period such as, for example, 10, 15, 20, 25, 30, etc. minutes. The user can initiate logic 902 upon depression (and/or multiple depression) of a designated button or other input. As described above, when in sleep or energy saver mode, nonessential functions/processes are suspended while others are not. And, as also described above, remote device 104 can be awoken by any user input (e.g., user depression of a button or other input). Hence, logic 902 can conserve and prolong the battery power/source of remote device 104.

Figure 10:
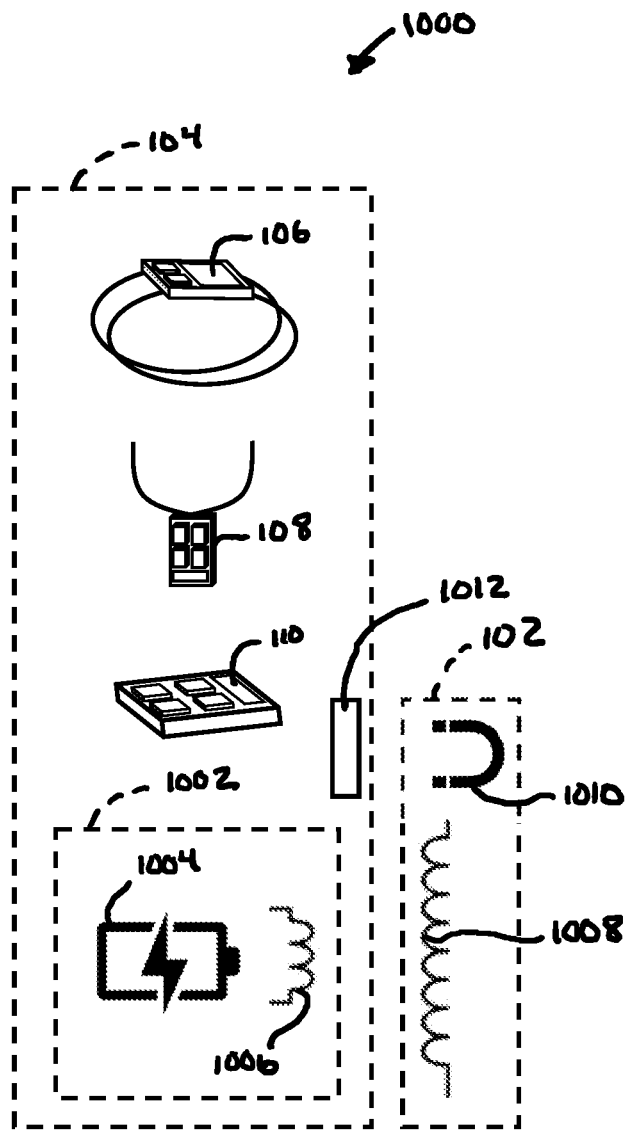
FIG. 10 is one embodiment of a system and method for a remote control and medical device having wireless charging capacity and functionality.

FIG. 10 illustrates one embodiment 1000 of a system and method for wirelessly charging remote device 104. Remote device 104 includes, for example, a charging circuit and logic 1002. Charging circuit and logic 1002 include a rechargeable power source 1004 such as, for example, a lithium ion (or similar) battery and a charging coil circuit 1006. Charging coil circuit 1006 uses a coil to convert an electric field into an electric current for charging the power source 1004.

Medical device 102 also includes a charging coil circuit 1008 for generating an electric field to be received and used by remote device 104 in the wireless charging process. Charging coil circuit 1008 uses a coil to generate an electric field that can be received by charging coil circuit 1006 of remote device 104. Charging coil circuit 1008 obtains power from the power source of medical device 102, which can be either a wall source (e.g., AC) or battery power (e.g., DC) source. The electric field generated by charging coil circuit 1008 induces a current (or flow of electricity) in the charging coil circuit 1006, which is used to charge power source 1004. In this manner, the charging coil of remote 104 and the charging coil of medical device 102 are inductively coupled together allowing transfer of power between the two devices for recharging power sources such as, for example, batteries.

The system and method 1000 can also include a magnetic coupling arrangement in order to maintain remote device 104 in the proper physical charging position and orientation with respect to the wireless charging location on the external housing of medical device 102. In one embodiment, remote device 104 includes within its housing a metallic (or magnetic) component 1012. Medical device 102 can include within its housing a magnet (or electromagnet) 1010. In operation, as remote device 104 is brought closer to the location of the wireless charging area on the housing of medical device 102, metallic component 1012 will be drawn to magnet 1010 thereby allowing the respective charging coils of each device to be properly aligned and oriented for the wireless charging process. Magnet 1010 can be any shape including circular, segmented (e.g., segmented circle, ellipse, polygon, etc.) linear, etc. Metallic component 1012 can also be of any shape but preferably of complementary shape to magnet 1010. Moreover, the physical charging location on the housing of medical device 102 can be anywhere but preferably in a convenient location easily reachable by the user. This includes, for example, near the control panel (e.g., above, below, to the side thereof, etc.) of medical device 102. On example location is on the top surface of the housing of medical device 102. Further, indicia or markings can be provided thereon to indicate to the user where is the location of the wireless charging station on medical device 102. Further, the wireless charging location on the housing of remote device 104 can be in any location, but preferably in the reverse or backside of the housing to allow close physical contact or proximity with the wireless charging station/location on the housing of medical device 102. In a further embodiment, the charging location can be a pocket formed in the housing that would allow at least partial insertion of the remote device 104 to properly position it for wireless or wired (via a quick connect/disconnect port) charging. The pocket can be located at any convenient location on the housing including front, top and sides thereof.

Remote device 104 and medical device 102 can further include, for example, circuitry and logic (e.g., 1002) for detecting the presence of a device or electric field suitable for wireless charging purposes and initiating the charging process to the rechargeable power source (e.g., 1004). Further circuitry and logic can be included therein, for example, to monitor and display the progress of the recharging process including displaying the estimated charge of the power source (e.g., percent charged) and to discontinue the recharging process when capacity has been reached in order to not damage the rechargeable power source. This can be displayed on the display(s) of the remote device 104 and/or medical device 102.

Figure 11:
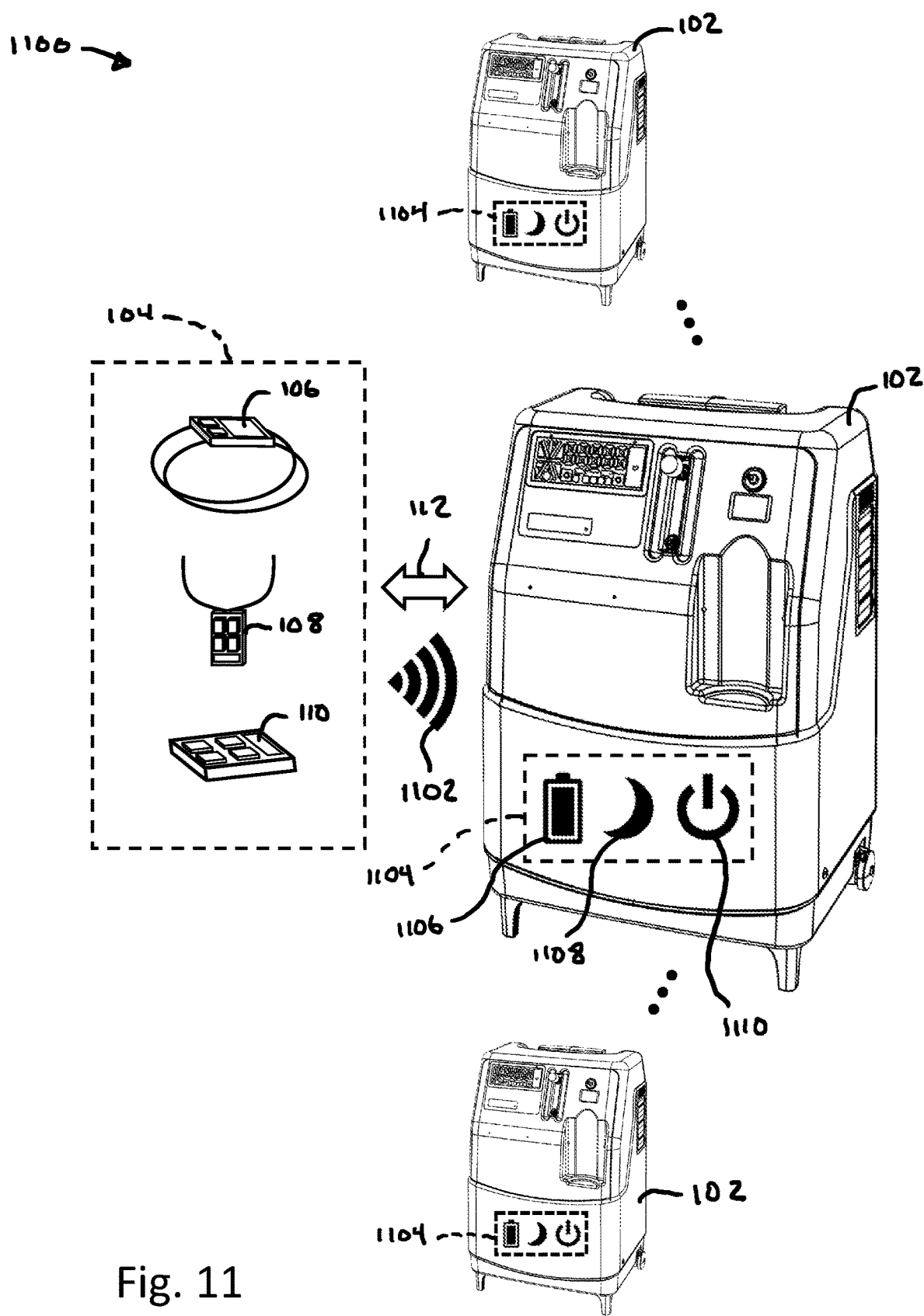
FIG. 11 is one embodiment of a system and method for a remote control and medical device having provider or warehouse/storage modes and functionality for awakening and/or pairing remote controls to medical devices.

Referring now to FIG. 11, one embodiment of a system and method 1100 for awakening or identifying a medical device 102 is shown. In a warehouse environment, there may be many medical devices 102 stored. And, the respective remote devices 104 may have become physically separated from their respective medical devices. Medical device(s) 102 include logic and circuitry 1104 for awakening when its remote device 104 sends signal 1102. In this manner, a signal from remote device 104 can be used to waken and thereby identify which medical device 102 is associated therewith and the two units can be physically associated again.

In one embodiment, medical device 102 includes a power source (e.g., battery) 1106, sleep logic 1108, and wake logic 1110. Battery 1106 allows medical device 102 to run in low power mode whereby sleep logic 1108 and wake logic 1110 are active but all other non-essential functions and processes are off. Thus, sleep logic 1108 can be active even though medical device 102 is unplugged for a wall source of power such as when, for example, medical device 102 is at a warehouse. Sleep logic 1108 powers down the medical device 102 into a sleep state, which is not a completely off or powered down state. In one embodiment, sleep logic 1108 monitors for an off signal received either through remote device 104, input on the control panel of medical device 102, or internal sleep timer. When such a signal is received, sleep logic 1108 powers down all non-essential functions and processes as previously described herein.

Awake logic 1110 is not powered down, but instead repeatedly or continually monitors for receipt of a signal from the remote device 104 that is paired with the medical device 102. Upon receipt of such a signal, awake logic can, for example, light or flash an indicator lamp and/or generate an audio signal identifying which medical device 102, out of a plurality of medical devices 102, are controlled by that particular remote device 104. In other embodiments, awake logic 1110 can fully power on medical device 102 in order to identify medical device 102 from a plurality of such devices. In yet other embodiments, awake logic 1110 can await the receipt of a unique "awake and identify" signal from remote device 104 instead of any input signal. The unique "awake and identify" signal can be generated by a special input (e.g., a uniquely designated button or other input) on remote device 104 if so desired.

So arranged, a remote device 104 can be used to identify its associated medical device 102 in, for example, a warehouse or storage environment containing a plurality of medical devices 102 (and even a plurality of remote devices) where the remote device may have become physically separated or otherwise unidentifiable with its associated medical device. Each medical device 102 in the plurality in the warehouse can include its own logic and circuitry 1104 for awakening when its remote device 104 sends signal 1102. This allows the two components to be physically associated again without having to replace or re-connect (e.g., pair) a new or different remote device 102 to the medical device 104 to make up for the lost one.

Figure 12:
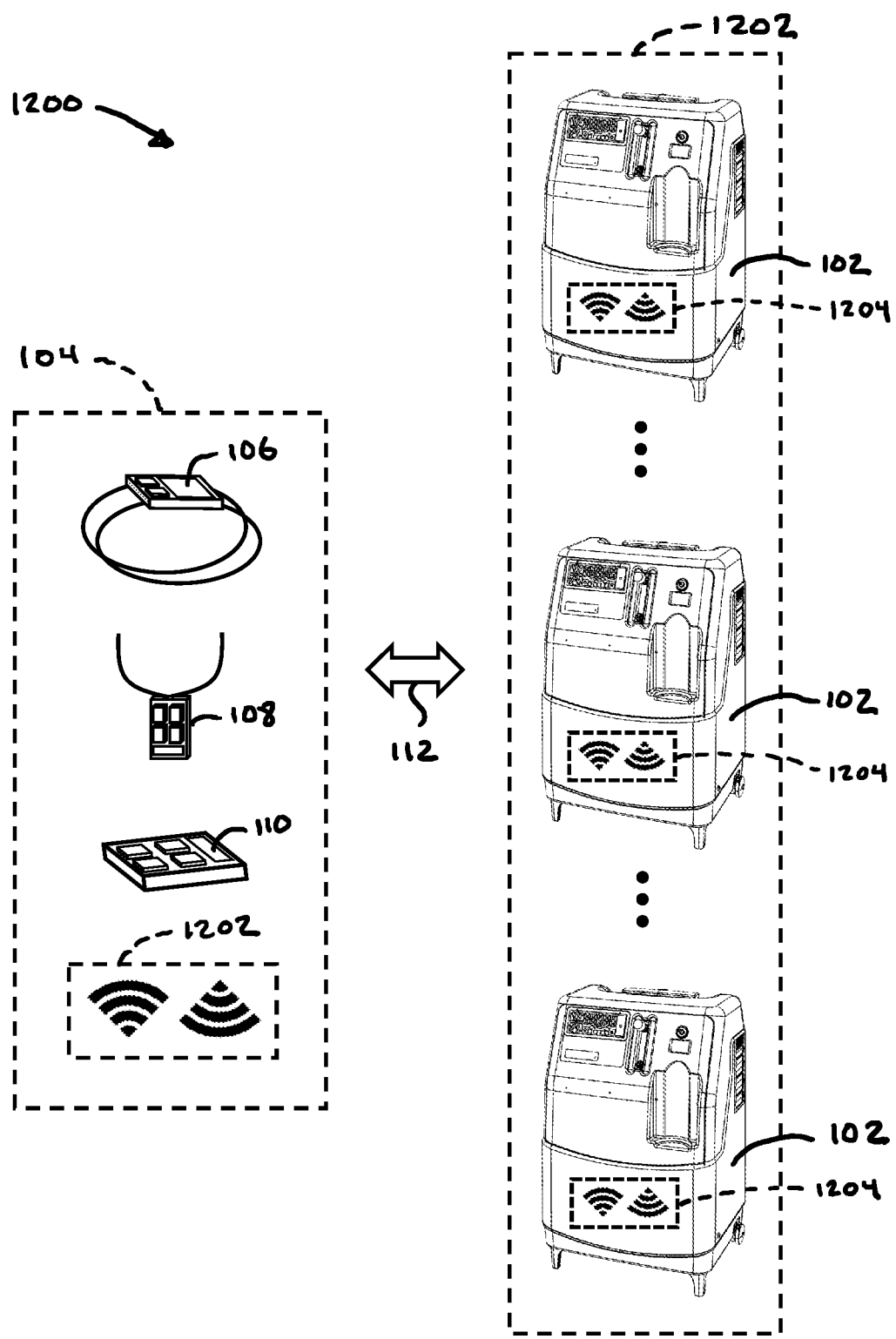
FIG. 12 is one embodiment of a system and method for a remote control and one or more medical devices having master remote/key functionality.

FIG. 12 illustrates one embodiment 1200 of a system and method for a remote device 104 acting as a master remote that can communicate with any one or more medical device(s) 104. There may be many situations where a remote device 104 may be lost from its associated medical device 102. In such situations, it may be helpful for a remote device 104 to be able to perform as a master remote device capable of communicating with the medical device whose own remote was lost. In other situations, it may be helpful to have a master remote device 104 capable of communication with any one or more medical device(s) 102. This eliminates the need for having to use each individual remote device for each medical device.

Still referring to FIG. 12, remote device 104 can act as a master remote device communicating 112 with one or more medical devices 1202. Example scenarios where this may be useful include at the manufacturing facility, provider warehouse, institutions (e.g., hospitals, assisted care/living, nursing, etc. facilities.) In these facilities, large numbers of medical devices 1202 may be present and the use of master remote device 104 by medical, technical and/or service professionals can promote efficiency (versus having to locate and use each individual remote device for each individual medical device).

In one embodiment, remote device 104 includes master logic 1202 that can include, for example, a master key or code. The master key or code can be transmitted 112 to one or more medical devices 102. Logic 1204 within each medical device 102 includes one or more corresponding master codes or keys stored in memory. When a master remote device 104 transmits 112 the master key or code to a medical device 102, medical device 102 compares the key or code to those in its memory. If they match, medical device 102 recognizes master remote device 104 and further receives input, instructions, and/or commands therefrom. Master remote device 104 can include a user input (e.g., button or other input) by which to activate the master key or code function.

In a further embodiment, the master remote device 104 may be programmed to respond to the user that it has detected a corresponding medical device 102 after transmitting a key or master key/code. In the case where the remote device 104 is searching among multiple physical areas (e.g., within a house, medical care facility, warehouse, etc.), or in an area with poor visibility to its contents, or where other occupants are intended to be left undisturbed, the remote device 104 will receive back a confirmation key, code, or message from medical device 102 that it has received the key or code and is present or near. The remote device 104 can then generate a signal or prompt that may be in the from visual, audio, tactile or other forms of feedback to the user of the remote device 104 indicating a medical device 102 has responded and is in the area.

Further, master remote device 104 can include a selector input that allows the user (e.g., a technician or service person) to select which of the plurality of medical devices 102 are to be controlled by the master remote device. Master remote device 104 can also be a standalone remote device not primarily intended for the user, but for technical and/or service personnel. In other embodiments, master remote device 104 includes the ability to pair with a plurality of medical devices 102 by exchanging pairing codes to valid their communication connection. These unique pairings can be saved in the memory of the master remote device 104 and then, through the selector input described above, any one of such paired medical device(s) can be selected for control. Thus, by any one of a plurality of embodiments, a remote device having a master key or code can be used to control one or more medical devices.

Figure 13:
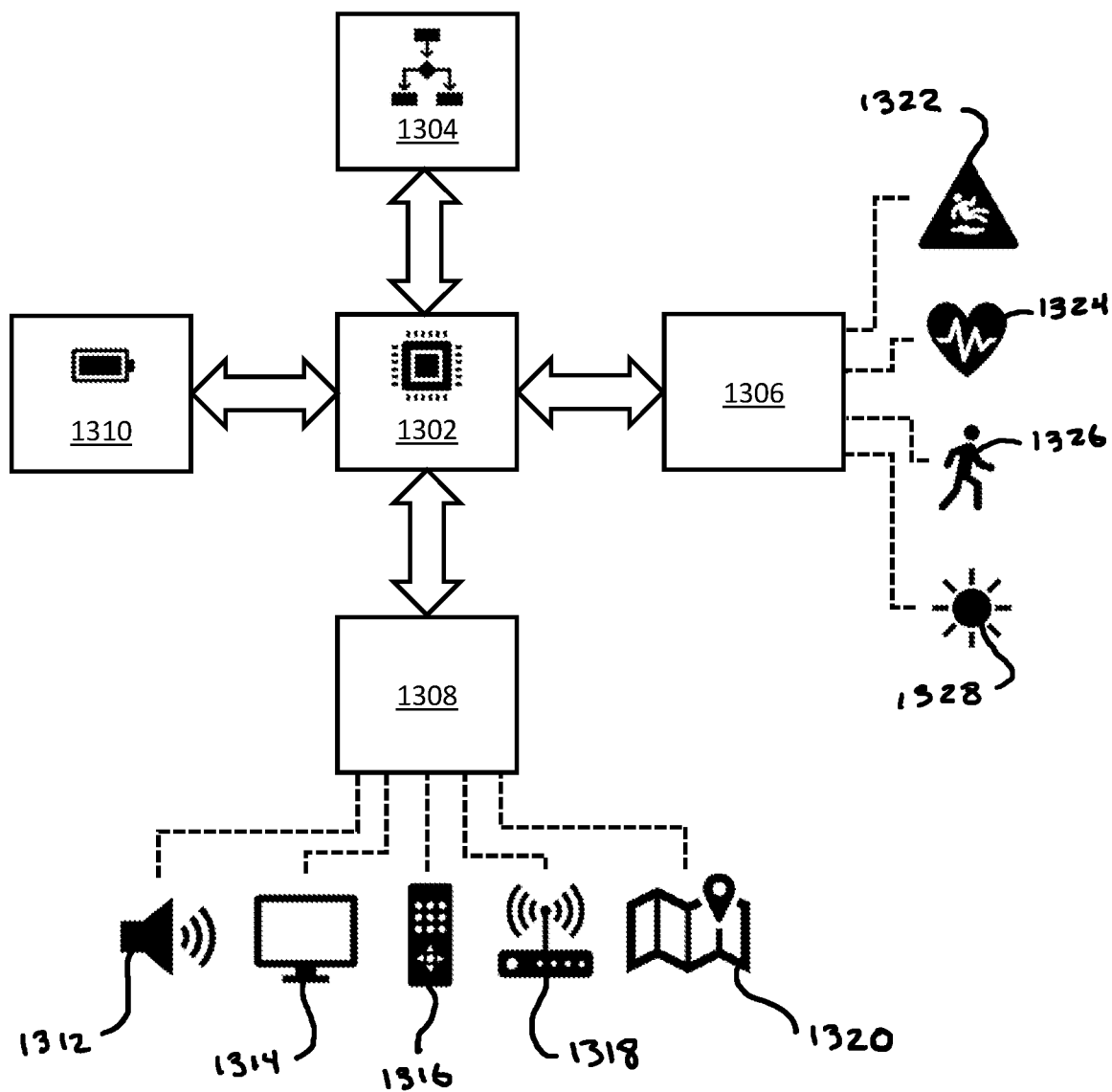
FIG. 13 illustrates various embodiments of remote control system components and functionality.

FIG. 13 illustrates one embodiment of a block diagram of a remote device 104. Remote device 104 includes a processing circuit 1302 having a microprocessor capable of executing instructions. A memory or storage circuit 1304 is provided for holding software logic, instructions and data which can be read and stored to by the processing circuit 1302. Remote device 104 can include, but does not need to, one or more sensors 1306 for providing information to the processing unit 1302. Also, remote device 104 includes one or more input/output devices 1308 and a power/batter circuit 1310 (including components and circuitry for wireless charging as previously disclosed.)

As previously described, one or more input/output devices 1308 can be used by remote device 104. This includes one or more audio device(s) 1312 (e.g., speaker, buzzer, etc.), visual/display device(s) 1314 (e.g., lights, lamps, displays (including touch displays), etc.), key(s)/button(s) 1316 (e.g., depressible or touch, etc.), radio-frequency transmitter(s) and/or receiver(s) 1318 (e.g., cellular, WiFi, Bluetooth, UHF, VHF, etc.), GPS radio/circuit 1320, etc. This listing is not intended to be exhaustive but only illustrative of input/output devices that can be used to accomplish the functions disclosed by the embodiments herein. Other input/output devices are intended to fall within the scope of the disclosure according to the functions disclosed by the embodiments.

Also previously described, one or more sensors 1306 can be used by remote device 104. This includes fall detector(s) 1322 (e.g., accelerometer(s), etc.) biosensors 1324 (e.g., EKG, blood pressure, blood oxygen concentration, respiratory, cardiac, etc.), activity 1326 sensor(s) (e.g., motion, movement, etc.), light sensor(s) 1328, etc. This listing is not intended to be exhaustive but only illustrative of sensor devices that can be used to accomplish the functions disclosed by the embodiments herein. Other sensor devices are intended to fall within the scope of the disclosure according the functions disclosed by the embodiments.

Figure 14:
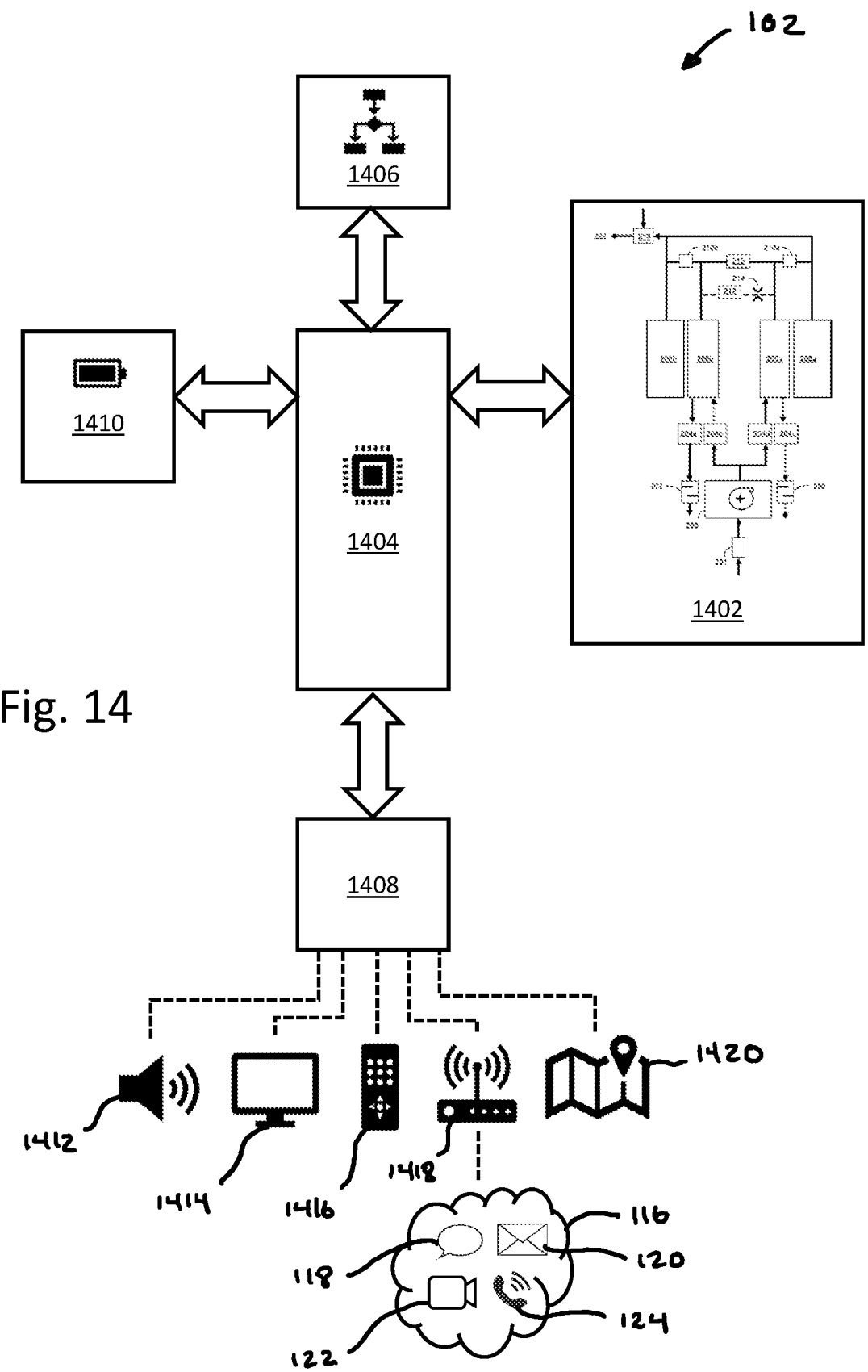
FIG. 14 illustrates various embodiments a medical device system components and functionality.

FIG. 14 illustrates one embodiment of a block diagram of a medical device 102. Medical device 102 includes a processing circuit 1404 having a microprocessor capable of executing instructions. A memory or storage circuit 1406 is provided for holding software logic, instructions and data which can be read and stored to by the processing circuit 1404. Medical device 102 also includes one or more input/output devices 1408 and a power/battery circuit 1410 (including components and circuitry for wireless charging and sleep and awake functions as previously disclosed.) Medical device 102 also includes medical device components 1402 for providing therapy or treatment to the user that is under control of processing circuit 1404. In the case of a medical oxygen concentrator, device components 1402 include a gas separation system that separates nitrogen from oxygen and provides the oxygen to a user. Examples of such systems have been described above and incorporated by reference. A medical oxygen concentrator is just one example and other medical device(s) are intended to fall within the scope of the disclosure including, for example, motorized/adjustable beds, CPAP devices, ventilators, etc.

As previously described herein, one or more input/output devices 1408 can be used by medical device 102. This includes one or more audio device(s) 1412 (e.g., speaker, buzzer, etc.), visual/display device(s) 1414 (e.g., lights, lamps, displays (including touch displays), etc.), key(s)/button(s) 1416 (e.g., depressible or touch, etc.), radio-frequency transmitter(s) and/or receiver(s) 1418 (e.g., cellular, WiFi, Bluetooth, UHF, VHF, etc.), GPS radio/circuit 1420, etc. The radio(s) 1418 can include modems for sending and receiving information to one or more cloud networks 116. This listing is not intended to be exhaustive but only illustrative of input/output devices that can be used to accomplish the functions disclosed by the embodiments herein. Other input/output devices are intended to fall within the scope of the disclosure according the functions disclosed by the embodiments.

Embodiments of remote device 104 and medical device 102 disclosed throughout this disclosure have been described as having various forms of logic to accomplish their functions. This logic is, for example, stored in memory 1304/1406 and executed by processing circuit 1302/1404.

The logic can be in the form of computer-readable and executable instructions that reside in software or firmware. The logic can also be implemented in digital logic circuits. Moreover, though the logic has been described in terms of sequence(s) of steps or processes, the order of those sequences can be changed while still obtaining the disclosed results. Hence, the logic descriptions herein are illustrative and can be implemented in any suitable manner and on any suitable software or logic platform.

While the present inventions have been illustrated by the description of embodiments thereof, and while the embodiments have been described in considerable detail, it is not the intention of the descriptions to restrict or in any way limit the scope of the inventions to such detail. Additional advantages and modifications will readily appear to those skilled in the art. Therefore, the inventions, in their broader aspects, are not limited to the specific details, the representative apparatus, and illustrative examples shown and described. Accordingly, departures can be made from such details without departing from the spirit or scope of the general inventive concepts.

What is claimed:

1. A system for medical therapy comprising:
    a therapeutic medical device;
    a remote control device communicating with the therapeutic medical device;
    at least one emergency notification generated in response to an input signal; and
    an output signal transmitting the emergency notification from the therapeutic medical device;
    logic for determining if a network connection exists to receive and transmit the output signal; and
    logic for generating at least one of visual and audio distress indicators on the therapeutic medical device if a network connection does not exist.

2. The system of claim 1 wherein the therapeutic medical device is an oxygen concentrator having a gas separation system for separating therapeutic oxygen gas from a mixture of gases.

3. The system of claim 1 wherein the input signal comprises a user-actuatable input signal on the remote device indicating an emergency and generated by a patient contact of at least one input device on the remote control device.

4. The system of claim 1 wherein the input signal comprises a sensor signal on the remote device indicating an emergency.

5. The system of claim 1 wherein the emergency notification comprises at least one of audio data, video data, GPS data, time data, email data, mobile app notifications, text messages, and combinations of the foregoing.

6. The system of claim 1 wherein the output signal comprises at least one of wired and wireless signal transmitters, and combinations of the foregoing.

7. The system of claim 1 wherein the output signal comprises at least one of audio, visual, and haptic outputs, and combinations of the foregoing.

8. The system of claim 1 wherein the remote device comprises at least one of handheld and wearable remote devices, and combinations of the foregoing.

9. The system of claim 1 wherein the remote device comprises at least one sensor for sensing a user's condition.

10. The system of claim 9 wherein the at least one sensor comprises at least one of body temperature, EKG, heart beat/rate/variability, blood pressure, blood oxygen concentration, breathing rate, activity level, respiratory flow rate, respiratory volume, and combinations of the foregoing.

11. A remote control for a therapeutic medical device comprising:
    a processor;
    a memory in communication with the processor;
    an input signal for generating an emergency notification; and
    an output signal for transmitting the emergency notification from the therapeutic medical device; and
    logic for determining if a network connection exists to receive and transmit the output signal; and
    logic for generating at least one of visual and audio distress indicators on the therapeutic medical device if a network connection does not exist.

12. The remote device of claim 11 wherein the input signal comprises a user-actuatable input on the remote device indicating an emergency and is generated by a patient contact of at least one input device on the remote control device.

13. The remote device of claim 11 wherein the input signal comprises a sensor signal on the remote device indicating an emergency.

14. The remote device of claim 11 wherein the emergency notification comprises at least one of audio data, video data, GPS data, time data, email data, mobile app notifications, text messages, and combinations of the foregoing.

15. The remote device of claim 11 wherein the input signal comprises at least one sensor measuring at least one of body temperature, EKG, heart beat/rate/variability, blood pressure, blood oxygen concentration, breathing rate, activity level, respiratory flow rate, respiratory volume and combinations of the foregoing.

16. A method for emergency notification comprising:
    providing a therapeutic medical device and a remote control device for communicating with the therapeutic device;
    reading an input signal for an emergency notification indication;
    generating an emergency notification;
    determining if a network connection exists to receive and transmit the output signal;
    generating at least one of visual and audio distress indicators on the therapeutic medical device if a network connection does not exist; and
    transmitting the emergency notification from the therapeutic medical device if a network connection exists.

17. The method of claim 16 wherein reading an input signal for an emergency notification indication comprises reading a user input indicating an emergency wherein this step comprises detecting a patient contact of at least one input device on the remote control device.

18. The method of claim 16 wherein reading an input signal for an emergency notification indication comprises reading a sensor signal indicating an emergency.

19. The method of claim 16 wherein generating an emergency notification comprises generating at least one of audio data, video data, GPS data, time data, email data, mobile app notifications, text messages, and combinations of the foregoing.

20. The method of claim 16 wherein transmitting the emergency notification comprises generating at least one of at least one of audio, visual, and haptic outputs, and combinations of the foregoing.

21. A system for medical therapy comprising:
    a therapeutic medical device;
    a remote control device communicating with the therapeutic medical device;

at least one emergency notification generated in response to an input signal; and
an output signal transmitting the emergency notification from the therapeutic medical device;
logic for determining if a network connection exists to receive and transmit the output signal; and
logic for generating at least one of visual and audio distress indicators on the therapeutic medical device if a network connection does not exist and an emergency notification was generated.

* * * * *